(12) United States Patent
Juarez Paz

(10) Patent No.: US 11,806,535 B2
(45) Date of Patent: Nov. 7, 2023

(54) NEUROMODULATION PROGRAMMING TOOLS FOR NEUROMODULATOR REPLACEMENT

(71) Applicant: Boston Scientific Neuromodulation Corporation, Valencia, CA (US)

(72) Inventor: Leon Mauricio Juarez Paz, Berlin (DE)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 140 days.

(21) Appl. No.: 17/084,049

(22) Filed: Oct. 29, 2020

(65) Prior Publication Data
US 2021/0128923 A1 May 6, 2021

Related U.S. Application Data

(60) Provisional application No. 62/928,696, filed on Oct. 31, 2019.

(51) Int. Cl.
*A61N 1/36* (2006.01)
*A61N 1/372* (2006.01)

(52) U.S. Cl.
CPC ..... *A61N 1/36189* (2013.01); *A61N 1/36153* (2013.01); *A61N 1/36157* (2013.01); *A61N 1/36185* (2013.01); *A61N 1/37247* (2013.01)

(58) Field of Classification Search
CPC ............ A61N 1/37288; A61N 1/37235; A61N 1/37252; A61N 1/37254; A61N 1/37264
See application file for complete search history.

(56) References Cited

U.S. PATENT DOCUMENTS

| | | | | |
|---|---|---|---|---|
| 7,783,356 B2* | 8/2010 | Cazares | ............... | A61B 5/0031 607/30 |
| 8,554,331 B2* | 10/2013 | Gerber | ............... | A61N 1/36071 607/46 |
| 2012/0109238 A1* | 5/2012 | Patel | .................. | A61N 1/37252 607/32 |
| 2016/0339259 A1 | 11/2016 | Davis et al. | | |
| 2017/0361104 A1 | 12/2017 | Carcieri et al. | | |

* cited by examiner

*Primary Examiner* — George R Evanisko
(74) *Attorney, Agent, or Firm* — Schwegman Lundberg & Woessner, P.A.

(57) ABSTRACT

A system may be used with a first neuromodulator of a first neuromodulator type and a second neuromodulator of a second neuromodulator type where the first neuromodulator is programmed with a first set of modulation parameter settings. The system may comprise an input configured for receiving the first set of modulation parameter settings for the first neuromodulator type, a processor configured to execute a programmed set of instructions to determine a second set of modulation parameter settings for the second neuromodulator type based on the first set of modulation parameter settings for the first neuromodulator type, and an output configured present the second set of modulation parameter settings for entering into a neuromodulator programmer. The neuromodulator programmer may be configured to program the second neuromodulator with the second set of modulation parameters.

20 Claims, 16 Drawing Sheets

Lead Configuration

Lead Configuration
2x4

I  II
3  11
2  10
1  9
0  8

Lead I
Location  STN
Hemishere  Left
Lead II
Location  STN
Hemishere  Right

Clear  (P)

NKG******* 37612

ConfigurationV01

Configuration

| Replaced IPG Model | Adapter to use | Vercise IPG Model |
|---|---|---|
| Activa RC 37612 | M8 | Vercise |

|  | Left hemisphere | Right hemisphere |
|---|---|---|
| Target | STN | STN |
| Initial contact | 0 | 8 |

NEUROMODULATION PROGRAMMING TOOLS FOR NEUROMODULATOR REPLACEMENT

CLAIM OF PRIORITY

This application claims the benefit of priority under 35 U.S.C. § 119(e) of U.S. Provisional Patent Application Ser. No. 62/928,696, filed on Oct. 31, 2019, which is herein incorporated by reference in its entirety.

TECHNICAL FIELD

The present disclosure relates generally to medical devices, and more particularly, to neuromodulation systems, devices, and methods.

BACKGROUND

Neuromodulation, also referred to as neurostimulation, has been proposed as a therapy for a number of conditions. Examples of neuromodulation include Spinal Cord Stimulation (SCS), Deep Brain Stimulation (DBS), Peripheral Nerve Stimulation (PNS), and Functional Electrical Stimulation (FES), Implantable neuromodulation systems have been applied to deliver such a therapy. An implantable neuromodulation system may include an implantable neuromodulator, which may also be referred to as an implantable pulse generator (IPG), and one or more implantable leads each including one or more electrodes. The implantable neuromodulator delivers neuromodulation energy through one or more electrodes placed on or near a target site in the nervous system. An external programming device is used to program the implantable neuromodulation with parameters controlling the delivery of the neuromodulation energy. For example, the neuromodulation energy may be delivered in the form of electrical pulses using parameters that specify spatial (where to stimulate), temporal (when to stimulate), and informational (patterns of pulses directing the nervous system to respond as desired) aspects of a pattern of pulses.

The neuromodulator may be electively replaced, or may be replaced because of the battery is near the end of life or because of other reasons. Neurosurgeons who are usually not very familiar with programming stimulation configurations usually replace neuromodulators without the support of neurologists. Field personnel for the manufacturer of the neuromodulator may assist by manually configuring the neuromodulator.

DBS neuromodulator replacements (e.g. DBS neuromodulator replacements j may involve systems with different technologies. For example, the replacement may involve replacing a voltage source system with a current source system or replacing a current source system with a voltage source system, or may involve replacing a single source system with a multiple source system or replacing a multiple source system with a single source system. For example, a single voltage source neuromodulator may be replaced with a multiple current source neuromodulator. An example of a multiple current source neuromodulator is a multiple independent current control (MICC) system, which may deliver constant current through each electrode regardless of impedances. For example, each electrical contact may be connected to its own current source that is capable of sourcing or sinking current and that is independent of the other current sources for other contacts. In contrast, current provided through electrodes for voltage control devices with only one voltage source are dependent on the electrode impedances. The systems may have different manufacturers.

Field representatives currently manually calculate the stimulation setting using their knowledge of Ohm's law, current density and contact mapping of both systems. The required time to complete the task is proportional to the complexity of the settings. However, there is no standardized way for determining the stimulation settings for the replacement neuromodulator.

SUMMARY

This Summary includes examples that provide an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

An example (e.g. Example 1) of subject matter (such as a system, a device, apparatus or machine) may be used with a first neuromodulator of a first neuromodulator type and a second neuromodulator of a second neuromodulator type where the first neuromodulator is programmed with a first set of modulation parameter settings. The subject matter may comprise an input configured for receiving the first set of modulation parameter settings for the first neuromodulator type, a processor configured to execute a programmed set of instructions to determine a second set of modulation parameter settings for the second neuromodulator type based on the first set of modulation parameter settings for the first neuromodulator type, and an output configured present the second set of modulation parameter settings for entering into a neuromodulator programmer, wherein the neuromodulator programmer is configured to program the second neuromodulator with the second set of modulation parameters.

In Example 2, the subject matter of Example 1 may optionally be configured such that the first set of modulation parameter settings includes contact polarity settings to define a first set of active electrodes on at least one implanted lead including polarity for each of the first set of active electrodes, and the second set of modulation parameter settings includes contact polarity settings to define a second set of active electrodes on the at least one implanted lead including polarity for each of the second set of active electrodes. The first neuromodulator may be configured to implement the programmed first set of modulation parameter settings to deliver electrical energy using the at least one implanted lead to provide a first modulation field, and the second neuromodulator may be configured to implement the second set of modulation parameter settings to deliver electrical energy using the at least one implanted lead to provide a second modulation field. The second set of modulation parameters may be determined such that the second modulation field has a similar size and shape to the first modulation field.

In Example 3, the subject matter of any one or any combination of Examples 1-2 may optionally be configured such that the first neuromodulator of the first neuromodulator type includes a voltage source configured for use in providing voltage source modulation, the second neuromodulator of the second neuromodulator type includes a current source configured for use in providing current source modulation, and the second set of modulation parameter settings for the current source modulation is determined based on the first set of modulation parameter settings for the voltage source modulation.

In Example 4, the subject matter of Example 3 may optionally be configured such that the first neuromodulator of the first neuromodulator type has one voltage source configured for use in providing voltage source modulation, and the second neuromodulator of the second neuromodulator type includes multiple current sources configured for use to in providing current source modulation.

In Example 5, the subject matter of any one or any combination of Examples 1-4 may optionally be configured such that the first set of modulation parameter settings includes more than one anode or more than one cathode.

In Example 6, the subject matter of any one or any combination of Examples 1-5 may optionally be configured such that the subject matter includes a tablet or phone that includes the processor, and the tablet or phone is configured to implement an app to determine a second set of modulation parameter settings for the second neuromodulator type based on the first set of modulation parameter settings for the first neuromodulator type.

In Example 7, the subject matter of any one or any combination of Examples 1-5 may optionally be configured such that the subject matter includes a personal computer that includes the processor configured to implement a program to determine a second set of modulation parameter settings for the second neuromodulator type based on the first set of modulation parameter settings for the first neuromodulator type.

In Example 8, the subject matter of any one or any combination of Examples 1-7 may optionally be configured such that the subject matter includes a user interface with at least one data entry field and configured to enable a user to enter at least one setting from the first set of parameter settings into the at least one data entry field, wherein the input includes the at least one setting entered by the user into the at least one data entry field.

In Example 9, the subject matter of Example 8 may optionally be configured such that the user interface is configured with at least one data entry field for receiving model information for the first neuromodulator and model information for the second neuromodulator.

In Example 10, the subject matter of any one or any combination of Examples 8-9 may optionally be configured such that the user interface is configured with at least one data entry field for receiving contact configuration data.

In Example 11, the subject matter of any one or any combination of Examples 8-10 may optionally be configured such that the user interface is configured with at least one data entry field for receiving contact impedance data.

In Example 12, the subject matter of any one or any combination of Examples 8-11 may optionally be configured such that the user interface is configured with at least one data entry field for receiving therapy values.

In Example 13, the subject matter of any one or any combination of Examples 1-12 may optionally be configured such that the input includes a camera for capturing an image from a programmer screen for a programmer of the first neuromodulator. The programmer screen may include at least one setting for the first set of modulation parameter settings, and the system may be configured to automatically recognize the at least one setting from the image and use the at least one setting from the image in determining the second set of modulation parameter settings for the second neuromodulator type.

In Example 14, the subject matter of any one or any combination of Examples 1-13 may optionally be configured such that the output includes a display configured to present the second set of modulation parameter settings to a user for use by the user for entering into the neuromodulator programmer.

In Example 15, the subject matter of any one or any combination of Examples 1-14 may optionally be configured such that the output includes a wireless communication transceiver configured for wirelessly communications with the neuromodulator programmer. The second set of modulation parameter settings may be wirelessly communicated to the neuromodulator programmer.

An example (e.g. Example 16) of subject matter (e.g. a method, a means for performing acts, or a machine-readable medium including instructions that, when performed by the machine, cause the machine to perform acts) may be performed using a first neuromodulator of a first neuromodulator type and a second neuromodulator of a second neuromodulator type where the first neuromodulator is programmed with a first set of modulation parameter settings. The subject matter may include receiving the first set of modulation parameter settings for the first neuromodulator type, determining, using a processor configured to execute a programmed set of instructions, a second set of modulation parameter settings for the second neuromodulator type based on the first set of modulation parameter settings for the first neuromodulator type, and presenting the second set of modulation parameter settings for entering into a neuromodulator programmer, wherein the neuromodulator programmer is configured to program the second neuromodulator with the second set of modulation parameters.

In Example 17, the subject matter of Example 16 may optionally be configured such that the first set of modulation parameter settings includes contact polarity settings to define a first set of active electrodes on at least one implanted lead including polarity for each of the first set of active electrodes, and the second set of modulation parameter settings includes contact polarity settings to define a second set of active electrodes on the at least one implanted lead including polarity for each of the second set of active electrodes. The first neuromodulator may be configured to implement the programmed first set of modulation parameter settings to deliver electrical energy using the at least one implanted lead to provide a first modulation field. The second neuromodulator may be configured to implement the second set of modulation parameter settings to deliver electrical energy using the at least one implanted lead to provide a second modulation field. The determining the second set of modulation parameter settings may include determining the second set of modulation parameter settings that cause the second modulation field to have a similar size and shape to the first modulation field.

In Example 18, the subject matter of any one or any combination of Examples 16-17 may optionally be configured such that the first neuromodulator of the first neuromodulator type includes a voltage source configured for use in providing voltage source modulation, the second neuromodulator of the second neuromodulator type includes a current source configured for use in providing current source modulation, and the determining the second set of modulation parameter settings for the current source modulation is determined based on the first set of modulation parameter settings for the voltage source modulation.

In Example 19, the subject matter of Example 18 may optionally be configured such that the first neuromodulator of the first neuromodulator type has one voltage source configured for use in providing voltage source modulation, and the second neuromodulator of the second neuromodulator type includes multiple current sources configured for use to in providing current source modulation.

In Example 20, the subject matter of any one or any combination of Examples 16-19 may optionally be configured such that the first set of modulation parameter settings include more than one anode or more than one cathode.

In Example 21, the subject matter of any one or any combination of Examples 16-20 may optionally be configured such that the determining the second set of modulation parameter settings includes implementing an app on a tablet or a phone to determine the second set of modulation parameter settings for the second neuromodulator type based on the first set of modulation parameter settings for the first neuromodulator type.

In Example 22, the subject matter of any one or any combination of Examples 16-21 may optionally be configured such that the determining the second set of modulation parameter settings includes implementing a program on a personal computer to determine a second set of modulation parameter settings for the second neuromodulator type based on the first set of modulation parameter settings for the first neuromodulator type.

In Example 23, the subject matter of any one or any combination of Examples 16-22 may optionally be configured such that the subject matter includes receiving via a user interface model identification for the first neuromodulator and model identification for the second neuromodulator.

In Example 24, the subject matter of any one or any combination of Examples 16-23 may optionally be configured such that the subject matter includes receiving via a user interface contact impedance data.

In Example 25, the subject matter of any one or any combination of Examples 16-24 may optionally be configured such that the receiving the first set of modulation parameter settings includes receiving via a user interface contact configuration data.

In Example 26, the subject matter of any one or any combination of Examples 16-25 may optionally be configured such that the receiving the first set of modulation parameter settings includes receiving via a user interface therapy values.

In Example 27, the subject matter of any one or any combination of Examples 16-26 may optionally be configured such that the receiving the first set of modulation parameter settings includes using a camera to capture an image from a programmer screen for a programmer of the first neuromodulator wherein the programmer screen includes at least one setting for the first set of modulation parameter settings, and automatically recognizing the at least one setting from the image and use the at least one setting from the image in determining the second set of modulation parameter settings for the second neuromodulator type.

In Example 27, the subject matter of any one or any combination of Examples 16-26 may optionally be configured such that the presenting the second set of modulation parameter settings for entering into a neuromodulator programmer includes presenting the second set of modulation parameter settings to a user via a display on a mobile device for use by the user for entering into the neuromodulator programmer, wherein the mobile device includes a phone or tablet or personal computer.

In Example 29, the subject matter of any one or any combination of Examples 16-28 may optionally be configured such that the presenting the second set of modulation parameter settings for entering into a neuromodulator programmer includes wirelessly communicating the second set of modulation parameter settings to the neuromodulator programmer.

An example (e.g. Example 30) of subject matter (e.g. non-transitory computer-readable storage medium including instructions which when executed using at least one processor within a system cause the system to perform acts, a means for performing acts, or a method) may implement a method using a first neuromodulator of a first neuromodulator type and a second neuromodulator of a second neuromodulator type where the first neuromodulator is programmed with a first set of modulation parameter settings, where the implemented method includes receiving the first set of modulation parameter settings for the first neuromodulator type, determining, using a processor configured to execute a programmed set of instructions, a second set of modulation parameter settings for the second neuromodulator type based on the first set of modulation parameter settings for the first neuromodulator type, and presenting the second set of modulation parameter settings for entering into a neuromodulator programmer, wherein the neuromodulator programmer is configured to program the second neuromodulator with the second set of modulation parameters.

In Example 31, the subject matter of Example 30 may optionally be configured such that the first set of modulation parameter settings includes contact polarity settings to define a first set of active electrodes on at least one implanted lead including polarity for each of the first set of active electrodes, and the second set of modulation parameter settings includes contact polarity settings to define a second set of active electrodes on the at least one implanted lead including polarity for each of the second set of active electrodes. The first neuromodulator may be configured to implement the programmed first set of modulation parameter settings to deliver electrical energy using the at least one implanted lead to provide a first modulation field. The second neuromodulator may be configured to implement the second set of modulation parameter settings to deliver electrical energy using the at least one implanted lead to provide a second modulation field. The determining the second set of modulation parameter settings may include determining the second set of modulation parameter settings that cause the second modulation field to have a similar size and shape to the first modulation field.

In Example 32, the subject matter of any one or any combination of Examples 30-31 may optionally be configured such that the first neuromodulator of the first neuromodulator type includes a voltage source configured for use in providing voltage source modulation, the second neuromodulator of the second neuromodulator type includes a current source configured for use in providing current source modulation, and the determining the second set of modulation parameter settings for the current source modulation is determined based on the first set of modulation parameter settings for the voltage source modulation.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 13B illustrates a two port lead configuration screen from a first programmer for a first neuromodulator and a therapy setup screen on the neuromodulation conversion programming tool for entering contact configuration values and therapy values.

FIG. 15A-15B illustrate examples for a one port system and a two port system for using direct conversion settings to determine modulation parameter values for the second neuromodulator.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

In various examples, the neuromodulation system may include an implantable device configured to deliver neuromodulation therapies, such as DBS, SCS and PNS including vagus nerve stimulation (VNS), and one or more external devices configured to program the implantable device for its operations and monitor the performance of the implantable device. While DBS is discussed as a specific example, the present subject matter may also be applied to neuromodulator replacements for other types of neuromodulation therapies.

It is desirable to streamline and standardize neuromodulator replacements (e.g. DBS neuromodulators) by calculating the stimulation settings that therapeutically similar to the pre-replacement settings. Streamlining and standardizing replacements is particularly beneficial for settings involving more than one cathode or anode, and/or settings involving multiple areas The system may determine one or more stimulation parameters to modulate a target. For example, if the neuromodulator is a MICC system, the system may determine a stimulation current and an electrical current fractionalization across a plurality of electrodes. The current fractionalization refers to current distribution among electrodes, and may be represented by percentage cathodic current, percentage anodic current, or off (no current allocation). Although current fractionalization is discussed in this document, it is to be understood that voltage or electrical energy may similarly be fractionalized among the electrodes, which may result in a particular spatial distribution of the stimulation field.

Figure 1:
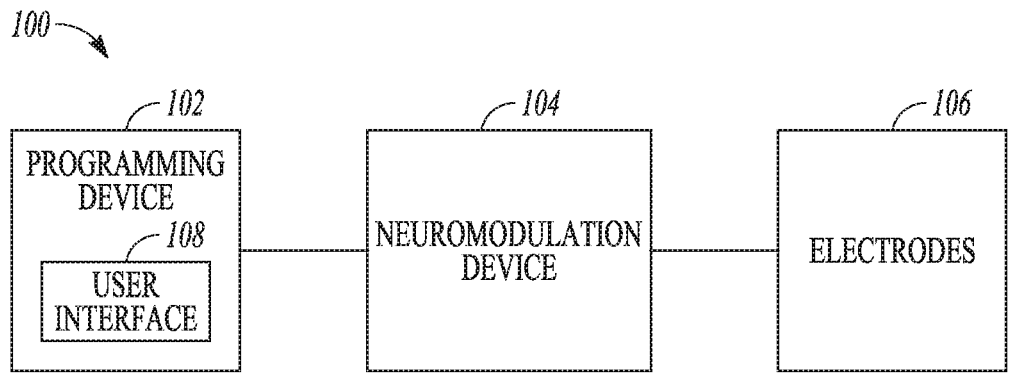
FIG. 1 illustrates, by way of example and not limitation, an embodiment of a neuromodulation system.

FIG. 1 illustrates, by way of example and not limitation, an embodiment of a neuromodulation system 100. The system 100 may, for example, be configured for DBS applications. The illustrated system 100 includes a programming device 102, a neuromodulation device 104, and electrodes 106. The electrodes 106 may be configured for placement on or near one or more neural targets in a patient. The stimulation device 104 may be configured to be electrically connected to the electrodes 106 and deliver neuromodulation energy, such as in the form of electrical pulses, to the one or more neural targets though the electrodes 106. In an example, the neuromodulation device 104 controls the delivery of neuromodulation energy according to a plurality of neuromodulation parameters, such as a selection of active electrodes for passing neuromodulation energy to the tissue, or stimulation pattern of the electrical pulses, among others. In various examples, at least some of the neuromodulation parameters are programmable by a user, such as a clinician.

The programming device 102 may be configured to be in communication with the neuromodulation device 104 via a wired or wireless link. The programming device 102 may provide the user with accessibility to user-programmable parameters. In the illustrated example, the programming device 102 may include a user interface 108 that allows a user to control the operation of the system 100 and monitor the performance of the system 100 as well as conditions of the patient including responses to the delivery of the neuromodulation. The user may control the operation of the system 100 by setting and/or adjusting values of the user-programmable parameters. In various examples, the user interface 108 may include a graphical user interface (GUI) that allows the user to create and/or edit graphical representations of various neuromodulation waveforms. The GUI may also allow the user to set and/or adjust neuromodulation fields each defined by a set of electrodes through which one or more electrical pulses represented by a waveform are delivered to the patient. The neuromodulation fields may each be further defined by the current fractionalization across the set of electrodes. In various examples, electrical pulses for a stimulation period (such as the duration of a therapy session) may be delivered to multiple neuromodulation fields.

In this document, a "user" includes a physician, other clinician, field representative or caregiver who treats the patient using the system 100; a "patient" includes a person who receives, or is intended to receive, neurostimulation via the system 100. In various examples, the patient may be allowed to adjust his or her treatment using system 100 to certain extent, such as by adjusting certain therapy parameters and entering feedback and clinical effect information.

Figure 2:
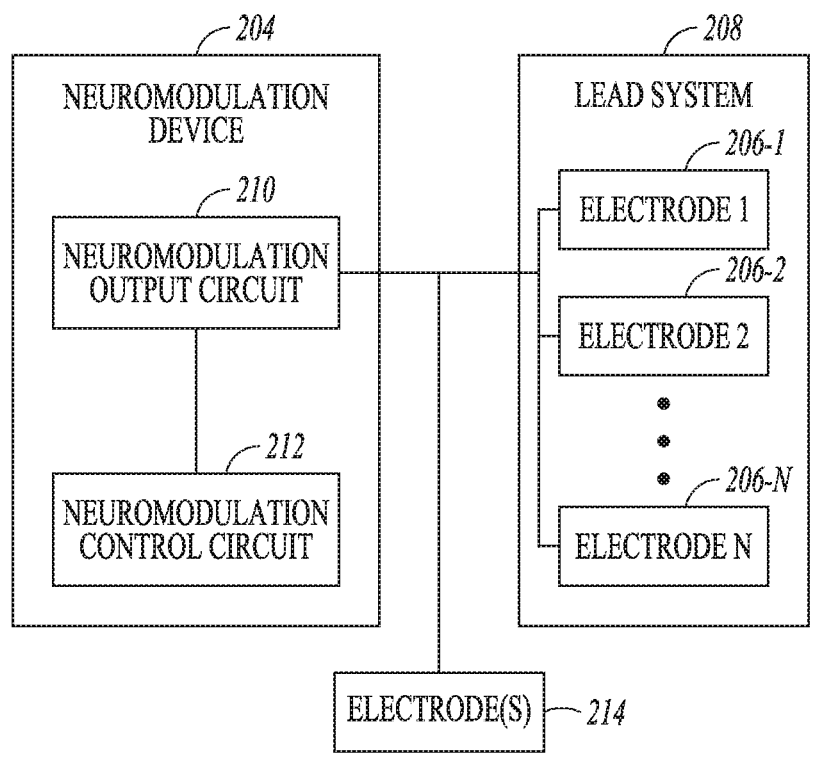
FIG. 2 illustrates, by way of example and not limitation, an embodiment of a stimulation device and a lead system, such as may be implemented in the neuromodulation system.

FIG. 2 illustrates, by way of example and not limitation, an embodiment of a stimulation device 204 and a lead system 208, such as may be implemented in the neuromodulation system 100. The neuromodulation device 204, also referred to as a neuromodulator, represents an embodiment of neuromodulation device 104, and includes a neuromodulation output circuit 210 and a neuromodulation control circuit 212. The neuromodulation output circuit 210 may produce and deliver electrical pulses. The neuromodulation control circuit 212 may control the delivery of the electrical pulses from the neuromodulation output circuit 210 according to a plurality of parameters. The lead system 214 includes one or more leads each configured to be electrically connected to neuromodulation device 204 and a plurality of electrodes (including electrode 206-1, 206-2, . . . , 206-N) distributed in the one or more leads. Each of the electrodes has an electrically conductive contact providing for an electrical interface between the neuromodulation output circuit 210 and patient tissue. The number of leads within the lead system, the number of electrodes on the leads, the leady types, and the type of electrodes (e.g. ring, segmented) may vary among the various embodiments.

The electrical pulses may be delivered from the neuromodulation output circuit 212 through a set of electrodes selected from the electrodes 206. In various examples, the electrical pulses may include one or more individually defined pulses, and the set of electrodes may be individually definable by the user for each of the individually defined pulses or each of collections of pulse intended to be delivered using the same combination of electrodes. In various examples, one or more additional electrodes 214 (referred to as reference electrodes) may be electrically connected to the neuromodulation device 204, such as one or more electrodes each being a portion of or otherwise incorporated onto a housing of the neuromodulation device 204. Electrodes on the housing may be referred to as "can electrodes". The neuromodulation may be delivered as a unipolar, bipolar, or multipolar stimulation. Monopolar stimulation uses a monopolar electrode configuration with one or more electrodes selected from the electrodes within the lead system 208 and at least one electrode from electrode(s) 214. Bipolar stimulation uses a bipolar electrode configuration with two electrodes selected from the electrodes within the lead system 208 and none of the electrode(s) 214. The bipolar stimulation may include balanced or unbalanced bipolar mode using a pair of electrodes on a lead, with the balancing current being applied to a reference electrode. Some bipolar stimulation may approximate a monopolar field, and thus may be considered to be a substantially monopolar field or a pseudo-monopolar field. By way of example and not limitation, a first electrode E1 may contribute 100% of the positive current, a second electrode E2 may contribute a small percentage of the negative current (e.g. <5%), and the can may contribute a large percentage of the negative current (e.g. 95%).

Figure 3:
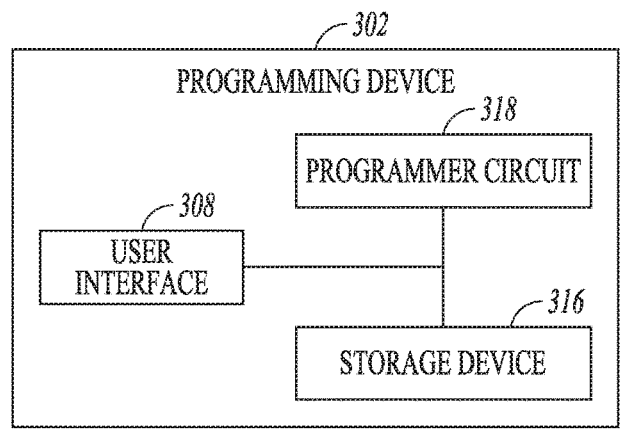
FIG. 3 illustrates, by way of example and not limitation, a programming device, which may be an embodiment of the programming device and implemented in neuromodulation system.

FIG. 3 illustrates, by way of example and not limitation, a programming device 302, which may be an embodiment of the programming device 102 and implemented in neuromodulation system 100. The programming device 302 may include a storage device 316, a programmer circuit 318, and a user interface 308. The programmer circuit 318 may be a part of control circuitry of the programming device 302, and is configured to support one or more functions allowing for programming of neuromodulation devices, such as neuromodulation device 104 including its various embodiments as discussed in this document. In various examples, the programmer circuit 318 may generate a plurality of neuromodulation parameters, collectively referred to as a neuromodulation configuration or neuromodulator settings, that control the deliver of the electrical pulses. In various examples, the neuromodulation configuration may specify a stimulation current (e.g., amplitude or energy of the stimulation) and an electrical current fractionalization across the plurality of electrodes. In some examples, the neuromodulation configuration may include a stimulation location and a stimulation current that corresponds to a metric value. In various examples, the neuromodulation configuration may include a virtual electrode state that specifies a virtual electrode type, location of the virtual electrode in a coordinate space, and stimulation current associated with virtual electrode voltage field and virtual electrode location. Electrical current fractionalization across a plurality of electrodes may be determined based on the voltage field of the virtual electrode.

The storage device 316 may store information used by the programmer circuit 318, including the neuromodulation configuration. The user interface 308 represents an embodiment of user interface 108, and may be coupled to the programmer circuit 318. In various examples, the user interface 308 may allow for definition of a pattern of electrical pulses for delivery during a neuromodulation therapy session by creating and/or adjusting one or more waveforms using a graphical method. The definition may also include definition of one or more neuromodulation fields each associated with one or more pulses in the pattern of electrical pulses. In various examples, the user interface 308 may include a GUI that allows the user to define the pattern pulses and perform other functions using graphical methods.

The circuits or subcircuits included in the neuromodulation system or devices, and their variations discussed in this document, may be implemented using a combination of hardware and software. For example, the circuits may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
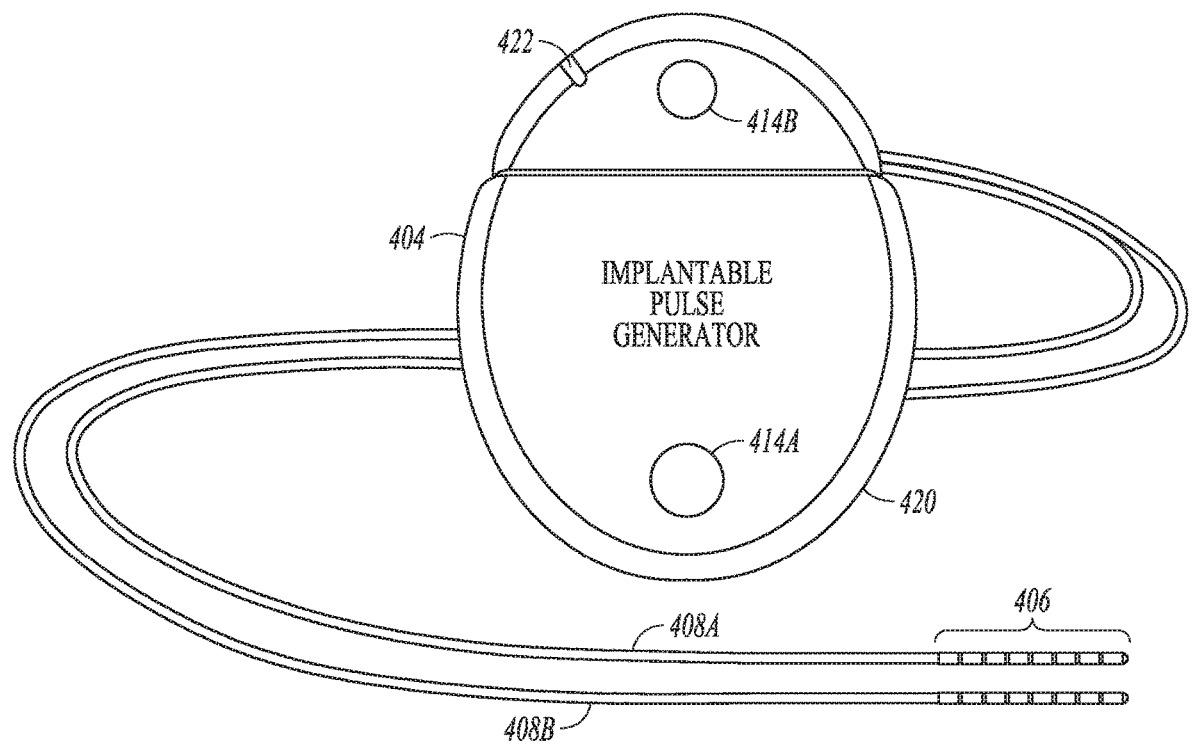
FIG. 4 illustrates, by way of example and not limitation, an embodiment of an implantable pulse generator (IPG) and an implantable lead system.

FIG. 4 illustrates, by way of example and not limitation, an embodiment of an implantable pulse generator (IPG) 404 and an implantable lead system, illustrated as two leads 408A and 408B. The IPG 404 represents an example implementation of neuromodulation device 204, and may include a hermetically-sealed IPG case 420 to house the electronic circuitry of IPG 404. The IPG 404 may include an electrode 414A and may include electrode 414B formed on the IPG case 420. The IPG 404 may include an IPG header 422 for coupling the proximal ends of leads 408A and 408B. Electrodes 426 and/or 428 may each be referred to as a reference electrode or can electrode. The IPG 404 may be communicatively coupled to a programming device, such as the programmer device 102 or the programming device 302, and configured to generate and deliver neuromodulation energy according to the neuromodulator configuration generated by the programming device 102 or 302.

The illustrated lead system includes, by way of example and not limitation, two implantable leads 408A and 408B. As illustrated in FIG. 4A, the IPG 404 may be coupled to the implantable leads 408A-B at a proximal end of each lead. The distal end of each lead includes electrical contacts or electrodes 406 for contacting a tissue site targeted for electrical neuromodulation. In various examples, one or more of the electrodes 406 may be column electrodes (also known as ring electrodes), or segmented electrodes circumferentially disposed on a directional lead such as 408A or 408B.

The implantable leads and electrodes may be shaped and sized to provide electrical neuromodulation energy to a neural target, such as a brain, a nerve target of a spinal cord, or a peripheral nerve target. Neuromodulation energy may be delivered in a unipolar mode between an electrode selected from electrodes 406 and another electrode selected from electrodes 414A and 414B, or in a balanced or unbalanced bipolar mode using a pair, or more, of electrodes on the same lead (e.g., lead 408A or lead 408B), with the balancing current being applied to reference electrodes 414A or 414B. Neuromodulation energy may be delivered in an extended bipolar mode using one or more electrodes of a lead (e.g., one or more electrodes of lead 408A) and one or more electrodes of a different lead (e.g., one or more electrodes of lead 408B).

The electronic circuitry of IPG 404 may include a control circuit that controls delivery of the neuromodulator energy. The control circuit may include a microprocessor, a digital signal processor, application specific integrated circuit (ASIC), or other type of processor, interpreting or executing instructions included in software or firmware. The neuromodulation energy may be delivered according to specified (e.g., programmed) modulation parameters. Examples of setting modulation parameters may include, among other things, selecting the electrodes or electrode combinations used in the neuromodulation, configuring an electrode or electrodes as the anode or the cathode for the neuromodulation, and specifying pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

The modulation parameters may additionally include fractionalization across electrodes. The fractionalization specifies distribution (e.g., the percentage) of the neuromodulation current, voltage, or electrical energy provided by an electrode or electrode combination, which affect the spatial distribution of the resultant neuromodulation field. In an example, current fractionalization specifies percentage cathodic current, percentage anodic current, or off (no current allocation). Current may be fractionalized across the active electrodes, such that active electrodes may receive a respective current percentage. Non-active electrodes are "off" or contribute no current to the neuromodulation. In the monopolar case, the fractionalized currents across the active electrodes add up to 100%. In the bipolar or multipolar cases, the fractionalized currents for at least one polarity add up to 100%, with any remaining percentage being allocated to the reference electrodes. Control of the current in terms of percentage allows precise and consistent distribution of the current among the electrodes even as the overall current amplitude for the parameter set is adjusted. In some examples, the current fractionalization may be defined by assigning an absolute current value (e.g., in milliampere, or mA) rather than a percentage to each electrode. Control of the current in terms of absolute values allows precise dosing of current through each specific electrode. It is suited for changing the current one contact at a time (and allows the user to do so) to shape the neuromodulation like a piece of clay (pushing/pulling one spot at a time).

The current fractionalization takes into account electrode/tissue coupling differences, which are the differences in how the tissue underlying each electrode reacts to electrical neuromodulation. In addition, electrodes on the distal portion of the lead may have lower gradient in the longitudinal direction, as electrical field strength may taper down at the ends of the lead. Current fractionalization may accommodate variation in the tissue underlying those electrodes. Various embodiments described herein implement a programmed algorithm to determine the appropriate fractionalization to achieve a desired neuromodulation field property.

Figure 5:
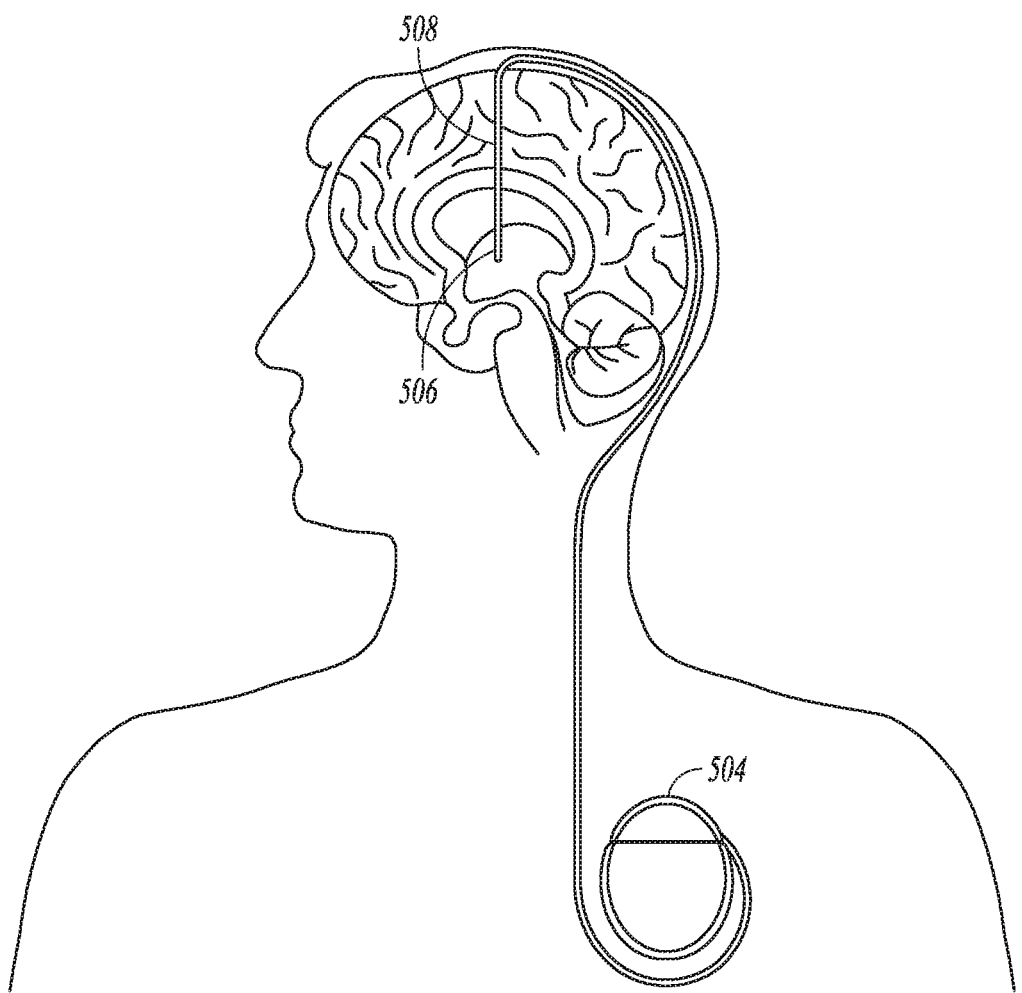
FIG. 5 illustrates, by way of example and not limitation, an embodiment of an IPG and an implantable lead system arranged to provide brain neuromodulation to a patient.

FIG. 5 illustrates, by way of example and not limitation, an embodiment of an IPG 504 and an implantable lead system 508 arranged to provide brain neuromodulation to a patient. An example of IPG 504 includes the IPG 404. The lead system 508 may include electrodes 506. An example of lead system 508 includes one or more of the leads 408A-B. An example of the electrodes 506 includes at least a portion of the electrodes 406. In the illustrated example, the IPG 504 and the implantable lead system 508 may provide DBS to a patient, with the neuromodulation target being neuronal tissue in a subdivision of the thalamus of the patient's brain. Other examples of DBS targets include neuronal tissue of the globus pallidus internus (GPi), the subthalamic nucleus (STN), the pedunculopontine nucleus (PPN), substantia nigra pars reticulate (SNr), cortex, globus pallidus externus (GPe), medial forebrain bundle (MFB), periaquaductal gray (PAG), periventricular gray (PVG), habenula, subgenual cingulate, ventral intermediate nucleus (VIM), anterior nucleus (AN), other nuclei of the thalamus, zona incerta, ventral capsule, ventral striatum, nucleus accumbens, white matter tracts connecting these and other structures. The DBS targets may also include regions determined analytically based on side effects or benefits observed in one or more patients, as well as regions specified by the user.

Figure 6:
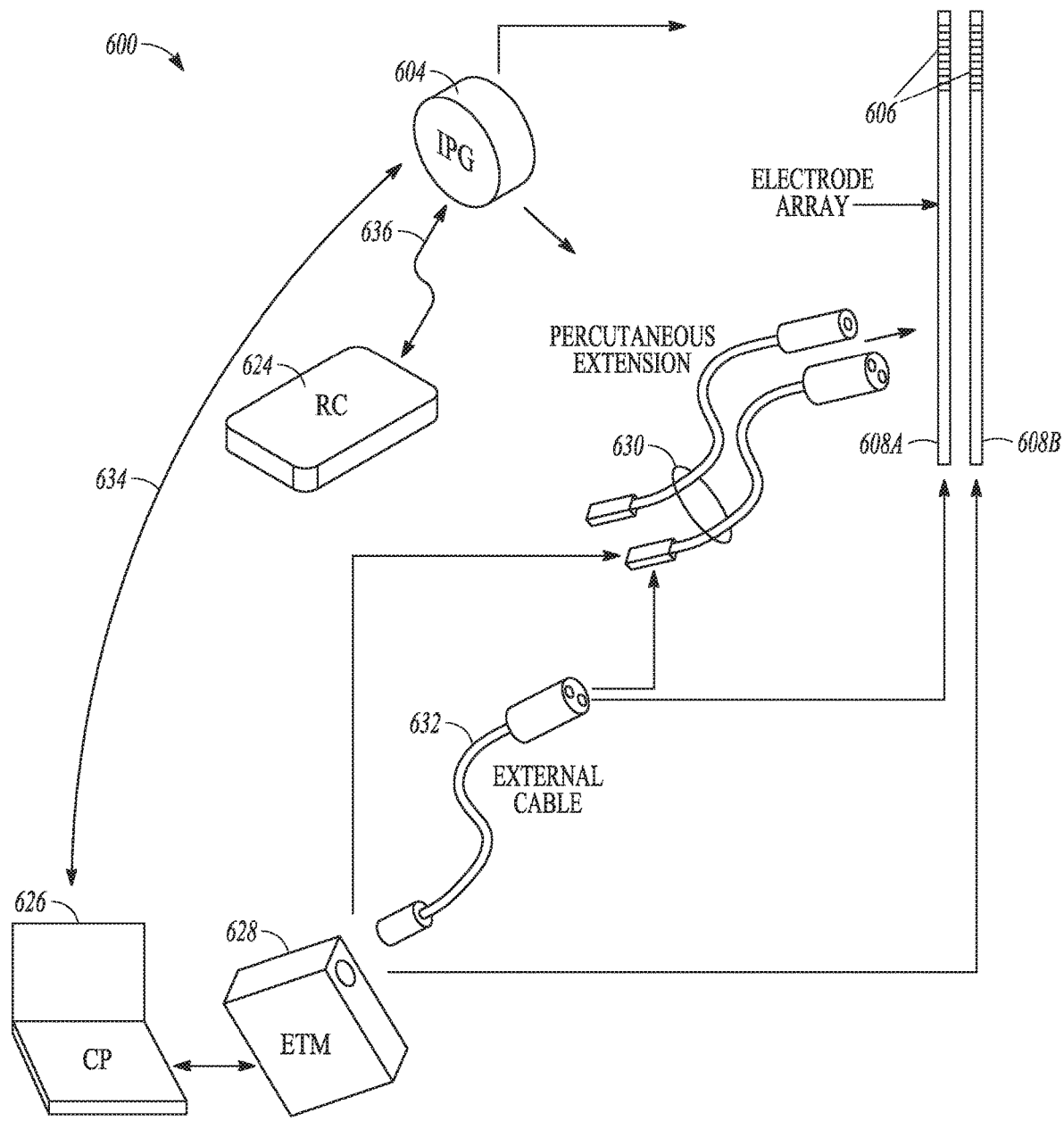
FIG. 6 illustrates, by way of example and not limitation, an embodiment of portions of a neuromodulation system.

FIG. 6 illustrates, by way of example and not limitation, an embodiment of portions of a neuromodulation system 600. The system 600 includes an IPG 604, implantable neuromodulation leads 608A and 608B, an external remote controller (RC) 624, a clinician's programmer (CP) 626, and an external trial modulator (ETM) 628. The system 600 may additionally include external sensors configured to sense one or more physiological parameters, such as a heart rate sensor, a pulse oximeter, an electrocardiogram sensor, an inertial sensor, or an electroencephalogram sensor, among others. The IPG 604 may be electrically coupled to the leads 608A and 608B directly or through percutaneous extension leads 630. The ETM 634 may be electrically connectable to the leads 608A and 608B via one or both of the percutaneous extension leads 630 and/or the external cable 632. The system 600 represents an embodiment of system 100, with IPG 604 representing an embodiment of the neuromodulation device 104, electrodes 606 of leads 608A and 608B representing the electrodes 106, and CP 626, RC 624, and the ETM 628 collectively representing the programming device 102.

The ETM 628 may be standalone or incorporated into the CP 630. The ETM 628 may have similar pulse generation circuitry as IPG 604 to deliver neuromodulation energy according to specified modulation parameters as discussed above. In an example, the ETM 628 is an external device and may be used as a preliminary stimulator after leads 408A and 408B have been implanted and used prior to stimulation with IPG 604 to test the patient's responsiveness to the stimulation that is to be provided by IPG 604. An external ETM 634 may be more easily configurable than the IPG 604.

The CP 626 may configure the neuromodulation provided by the ETM 628. If the ETM 628 is not integrated into the CP 626, then the CP 626 may communicate with ETM 628 using a wired connection (e.g., over a USB link) or by wireless telemetry such as using a wireless communications link. The CP 626 may also communicate with IPG 604 using a wireless communications link 634.

An example of wireless telemetry is based on inductive coupling between two closely-placed coils using the mutual inductance between these coils. This type of telemetry is referred to as inductive telemetry or near-field telemetry because the coils must typically be closely situated for obtaining inductively coupled communication. The IPG 604 may include the first coil and a communication circuit. The CP 626 may include or be otherwise electrically connected to the second coil such as in the form of a wand that may be place near the IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of r=$\lambda/2\pi$, where $\lambda$ is the wavelength of the transmitted electromagnetic energy. In one example, a communication range of an RF telemetry link is at least six feet but may be as long as allowed by the particular communication technology. RF antennas may be included, for example, in the header of the IPG 604 and in the housing of the CP 630, eliminating the need for a wand or other means of inductive coupling. An example is such an RF telemetry link is a Bluetooth® wireless link.

The CP 626 may be used to set modulation parameters for the neuromodulation after the IPG 604 has been implanted. This allows the neuromodulation to be tuned if the requirements for the neuromodulation change after implantation. The CP 626 may also upload information from or download information to the IPG 604.

The RC 624 also communicates with the IPG 604 using a wireless link 636. The RC 624 may be a communication device used by the user or given to the patient. The RC 624 may have reduced programming capability compared to the CP 626. This allows the user or patient to alter the neuromodulation therapy but does not allow the patient full control over the therapy. For example, the patient may be able to increase the amplitude of neuromodulation pulses or change the time that a preprogrammed stimulation pulse train is applied. The RC 624 may be programmed by the CP 626. The CP 626 may communicate with the RC 624 using a wired or wireless communications link. In some embodiments, the CP 626 is able to program the RC 624 when remotely located from the RC 624. In some examples, the RC 624 may download data to and upload data from the IPG 604.

Figure 7:
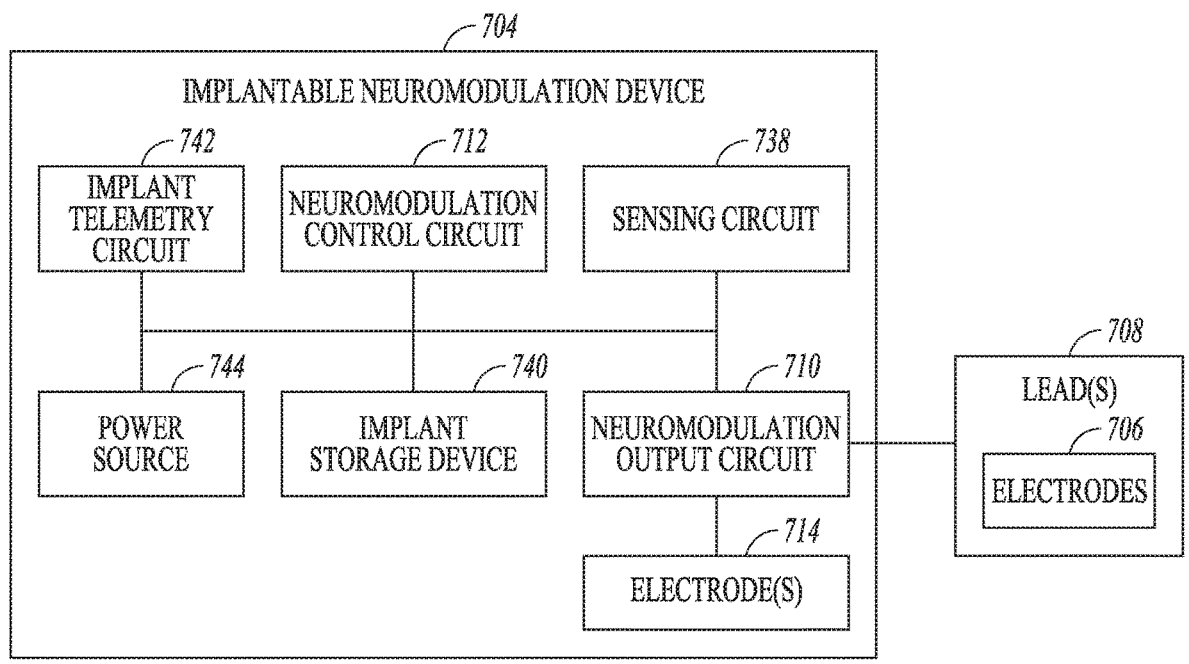
FIG. 7 illustrates, by way of example and not limitation, an embodiment of implantable neuromodulation device and one or more leads of an implantable neuromodulation system, such as the implantable system.

FIG. 7 illustrates, by way of example and not limitation, an embodiment of implantable neuromodulation device 704 and one or more leads 708 of an implantable neuromodulation system, such as the implantable system 600. The implantable neuromodulation device 704 represents an embodiment of stimulation device 104 or 204 and may be implemented, for example, as the IPG 604, Lead(s) 708 represents an embodiment of lead system 208 and may be implemented, for example, as implantable leads 608A-B. The lead(s) 708 includes electrodes 706, which represents an embodiment of electrodes 106 or 206 and may be implemented as electrodes 606. In some examples, the implantable stimulator 704 may additionally be communicatively coupled to one or more sensors configured to sense one or more physiological parameters, such as a heart rate sensor, a pulse oximeter, an electrocardiogram sensor, an inertial sensor, or an electroencephalogram sensor, among others. Sensors may include internal or external sensors.

The implantable neuromodulation device 704 may include a sensing circuit 738 when the stimulator needs a sensing capability, neuromodulation output circuit 710, a neuromodulator control circuit 712, an implant storage device 740, an implant telemetry circuit 742, a power source 744, and one or more electrodes 714. The sensing circuit 738, when included, may be configured to sense one or more physiologic signals for purposes of patient monitoring and/or feedback control of the neuromodulation. Examples of the physiologic signals include neural and other signals each indicative of a condition of the patient that is treated by the neuromodulation and/or a response of the patient to the delivery of the neuromodulation. The stimulation output circuit 212 is electrically connected to electrodes 706 through one or more leads 708 as well as electrodes 707, and delivers each of the neuromodulation pulses through a set of electrodes selected from electrodes 706 and electrode(s) 707. The device control circuit 712 represents an embodiment of device control circuit 212, and controls the delivery of the pulses according to the stimulation configuration (including stimulation parameters) received from the programming device 102 or 302. In one embodiment, the device control circuit 712 controls the delivery of the pulses using the one or more sensed physiologic signals. The implant telemetry circuit 744 provides the implantable stimulator 704 with wireless communication with another device, such as the CP 630 or the RC 632, including receiving values of the plurality of stimulation parameters from the other device. The implant storage device 746 stores the received stimulation configuration, including values of the plurality of stimulation parameters. The power source 748 provides the implantable stimulator 704 with energy for its operation. The power source 748 may include a battery. In one embodiment, the power source 748 includes a rechargeable battery and a battery charging circuit for charging the rechargeable battery. The implant telemetry circuit 744 may also function as a power receiver that receives power transmitted front an external device through an inductive couple. The electrode(s) 714 allow for delivery of the pulses in the monopolar mode or unbalanced bipolar mode. Examples of the electrode(s) 714 include electrode 414A and electrode 414B in IPG 404 as illustrated in FIG. 4A.

In an example, the implantable neuromodulation device 704 may be used as a database. A patient implanted with implantable neuromodulator 704 (such as may be implemented as IPG 604) may therefore carry patient information needed for his or her medical care when such information is otherwise unavailable. The implant storage device 740 may be configured to store such patient information. For example, the patient may be given a new RC 632 and/or travel to a new clinic where a new CP 630 is used to communicate with the device implanted in him or her. The new RC 632 and/or CP 630 may communicate with the implantable neuromodulator 704 to retrieve the patient information stored in implant storage device 740 through the implant telemetry circuit 744 and the wireless communication link 640, and allow for any necessary adjustment of the operation of the implantable neuromodulator 704 based on the retrieved patient information. The patient information be stored in the implant storage device 746 may include, for example, various types of neuromodulation settings. Examples may include positions of lead(s) 708 and electrodes 706 relative to the patient's anatomy (transformation for fusing computerized tomogram (CT) of post-operative lead placement to magnetic resonance imaging (MRI) of the brain), clinical effect data, objective measurements using quantitative assessments of symptoms (e.g., using microelectrode recording, accelerometers, and/or other sensors), and/or other information considered important or useful for providing adequate care for the patient. In various examples, the patient information to be stored in implant storage device 740 may include data transmitted to implantable stimulator 704 for storage as part of the patient information and data acquired by implantable neuromodulator 704, such as by using sensing circuit 742. The implant storage device 740 may be configured to store IPG model information, contact configuration, contact impedances, and/or therapy values for the programed neuromodulation therapy to be delivered by the implantable neuromodulator 704. This information may be stored in such a way as to be communicated with an external device such as a programmer, remote control, or an electronic device that is configured to function a neuromodulation conversion programming tool as is discussed in more detail below.

Figure 8:
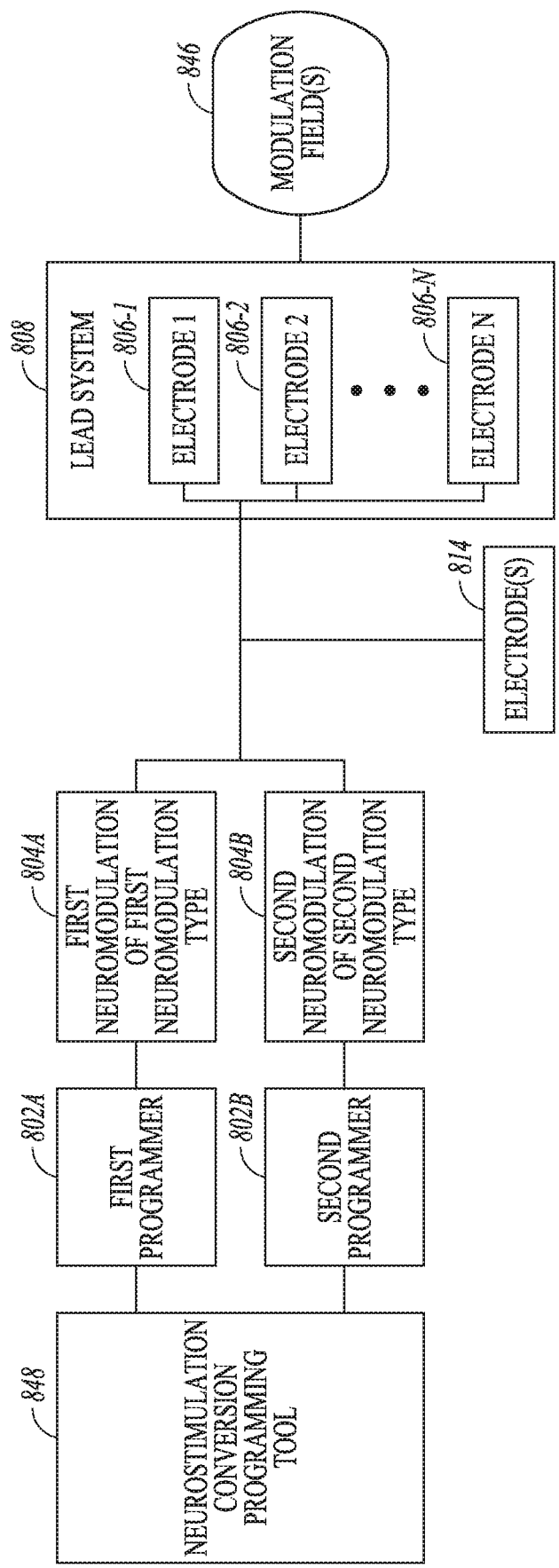
FIG. 8 illustrates, by way of example and not limitation, replacement of a first neuromodulator with a second neuromodulator.

FIG. 8 illustrates, by way of example and not limitation, replacement of a first neuromodulator with a second neuromodulator. Neuromodulators may be electively replaced, or may be replaced because of the battery is near the end of life or because of other reasons. The second neuromodulator may be a newer model with different capabilities and programming features. The neuromodulators may be of different types (e.g. different manufacturers, different models, different modulation technology, and different programming parameter(s)). For example, a voltage source neuromodulator may be replaced with a current source neuromodulator. In another example, a current source neuromodulator may be replaced with a voltage source neuromodulator. In an example, a single source neuromodulator may be replaced with a multiple source neuromodulator. In another example, a multiple source system may be replaced with a single source system. For example, a single voltage source neuromodulator may be replaced with a multiple current source neuromodulator. In a more specific example, the first neuromodulator may be a single voltage source neuromodulator and the second neuromodulator that is replacing the first neuromodulator may be a multiple current source neuromodulator (MICC).

The first neuromodulator 804A of a first neuromodulator type may be programmed with a neuromodulation parameter set by a first programmer 802A (e.g. clinical programmer 626 or remote control 624 illustrated in FIG. 6). The first neuromodulator 804A is connected to an implanted lead system 808 with a plurality of electrodes 806 (Electrodes 1-N). The first neuromodulator 804A is configured to deliver neuromodulation energy using the neuromodulation parameter set and the lead system to provide one or more neuromodulation fields 846 for a programmed neuromodulation therapy. The first neuromodulator 804A may be explanted and the second neuromodulator 804B of the second neuromodulator type may be implanted, and connected with previously-implanted lead system 808 and programmed with a neuromodulation parameter set using a second programmer 802B. Electrode(s) 814 may include an electrode(s) on the neuromodulators. Thus, there may be some differences in electrodes 814 because of the different neuromodulator types. Also, the replacement neuromodulation system may include an adapter 850. The adapter may connect the implantable pulse generator (IPG) to their extensions, which are connected to the implanted leads. The adapter may account for differences in pulses using a conversion factor, as the shape of pulses may not be the same for the different models of neuromodulators. For example, the area under a pulse curve may differ. The area under the curve generally corresponds to the amount of energy delivered to the neural tissue (e.g. the area under a current pulse curve is charge), and thus may be considered to be a dose.

Various embodiments of the present subject matter provide a neuromodulation conversion programming tool 848 that may be used to improve the programming of the second neuromodulator 804B to provide the modulation field(s) 846 of the same size and shape by converting parameter settings for the first neuromodulator 804A. The neuromodulation conversion programming tool 848 may be provided by a personal computer running software programs, or may be provided on a smartphone or tablet running a downloadable app that may be available from an app store. The neuromodulation conversion programming tool 848 may communicate with the programmer (e.g. clinician programmer) via a wireless network. For example, the wireless communication protocols may be implemented through a neuromodulation open source system. The neuromodulation open source system provides a communication interface that may be accessed by the neuromodulation conversion programming tool, but is not limited to any particular system.

Previous stimulation settings (e.g. contact polarity, voltage/current amplitude, pulse width and frequency) and impedance values may be collected prior to replacing the neuromodulator and entered into the tool. The values may be manually entered or automatically entered, or may be partially entered manually and partially entered automatically. The tool suggests stimulation settings that resemble the most the previous stimulation settings to achieve similar therapeutic effects. The therapeutic effects may include both spatial and temporal aspects. For example, the shape, size and orientation of the neuromodulation field(s) including location of anodic and cathodic loci within the field are spatial aspects of the delivered therapy. Therefore, the new stimulation settings may be selected to be similar to the shape and size of the modulation field(s) provided by the neuromodulator being replaced. However, the new stimulation settings may also be selected to provide similar temporal aspects (e.g. shape of waveform, timing of pulses, etc.). The camera of the smart phone, tablet or personal computer can be used to capture a screen image from the first programmer, and the captured image may be processed to automatically enter the previous stimulation data into the tool. The automatically-entered data may be reviewed and edited to verify that the automatically-entered data is correct.

Figure 9:
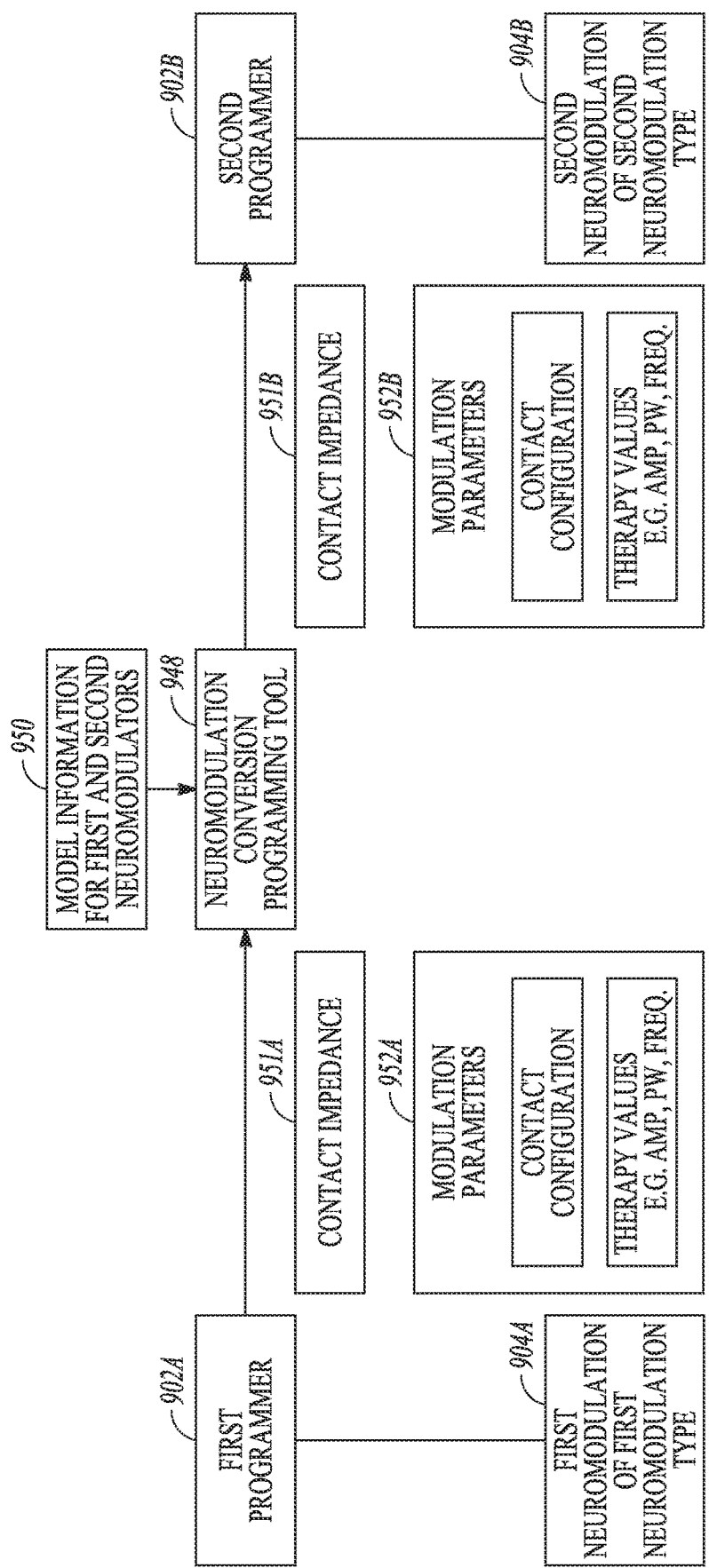
FIG. 9 illustrates, by way of example and not limitation, a process for entering information into the neuromodulation conversion programming tool, and outputs from the neuromodulation conversion programming tool.

FIG. 9 illustrates, by way of example and not limitation, a process for entering information into the neuromodulation conversion programming tool, and outputs from the neuromodulation conversion programming tool. For example, neuromodulation model information 950 (e.g. model number and/or name) for both the first and second programmer may be entered by the user through the user interface. In some embodiments, one or both of the neuromodulators may self-identify themselves (e.g. model information) to the tool. For example, the one or both of neuromodulators may respond to an inquiry from the neuromodulation conversion programming tool by identifying themselves. The neuromodulation tool 948 can be preprogrammed to various particularities for the model numbers (e.g. number and labeling of ports and electrodes, number and type of sources, etc.). The first programmer may display or otherwise communicate contact impedance information for the lead system. For example, in a voltage source system, the impedance information may be used along with Ohm's law to determine for a given voltage the amount of current that flows through the contacts to create the modulation field. The first programmer may display or otherwise communicate programmed modulation parameter information such as contact configuration and therapy values for the modulation signal. Example of contact configuration may include for each contact whether the contact is Off Anodic, or Cathodic. Furthermore, the contact configuration may include fractionalization values for the contacts (e.g. percent of anodic current or percent or cathodic current). The total amount of anodic energy (e.g. current) for all contacts is equal to 100% and the total of all cathodic energy (e.g. current) for all contacts is equal to 100%. The therapy values may include values defining the signal used to deliver the neuromodulation therapy. Examples of such values may include amplitude, pulse width, frequency, duty cycle, number of pulses in a burst, burst duration, burst frequency and the like. The neuromodulation conversion programming tool processes this data to communicate converted values to the second programmer. Examples of converted values may include values for contact configuration and therapy values (e.g. contact, impedance, and modulation parameters) to be implemented in the second neuromodulator 904B of the second neuromodulator type. The conversion will be appropriate for converting between the different types of neuromodulators (e.g. single voltage source neuromodulator to a multiple current source (MICC) neuromodulator in a manner that substantially maintains the spatial and temporal aspects of the therapy. The spatial aspects may include the size, shape and orientation of the modulation field(s) that was (were) generated by the first neuromodulator. The spatial aspects may include the cathodic or anodic loci within the modulation field(s). Temporal aspects may include shape of waveform, timing of pulses, and the like. Informational aspects, such as patterns of pulses directing the nervous system to respond as desired, may also be mimicked. Thus, a neuromodulation conversion programming tool enables the second neuromodulator to be initially with modulation parameters that are therapeutically effective, such that a subsequent therapy titration process may be quicker and more effective.

Figure 10:
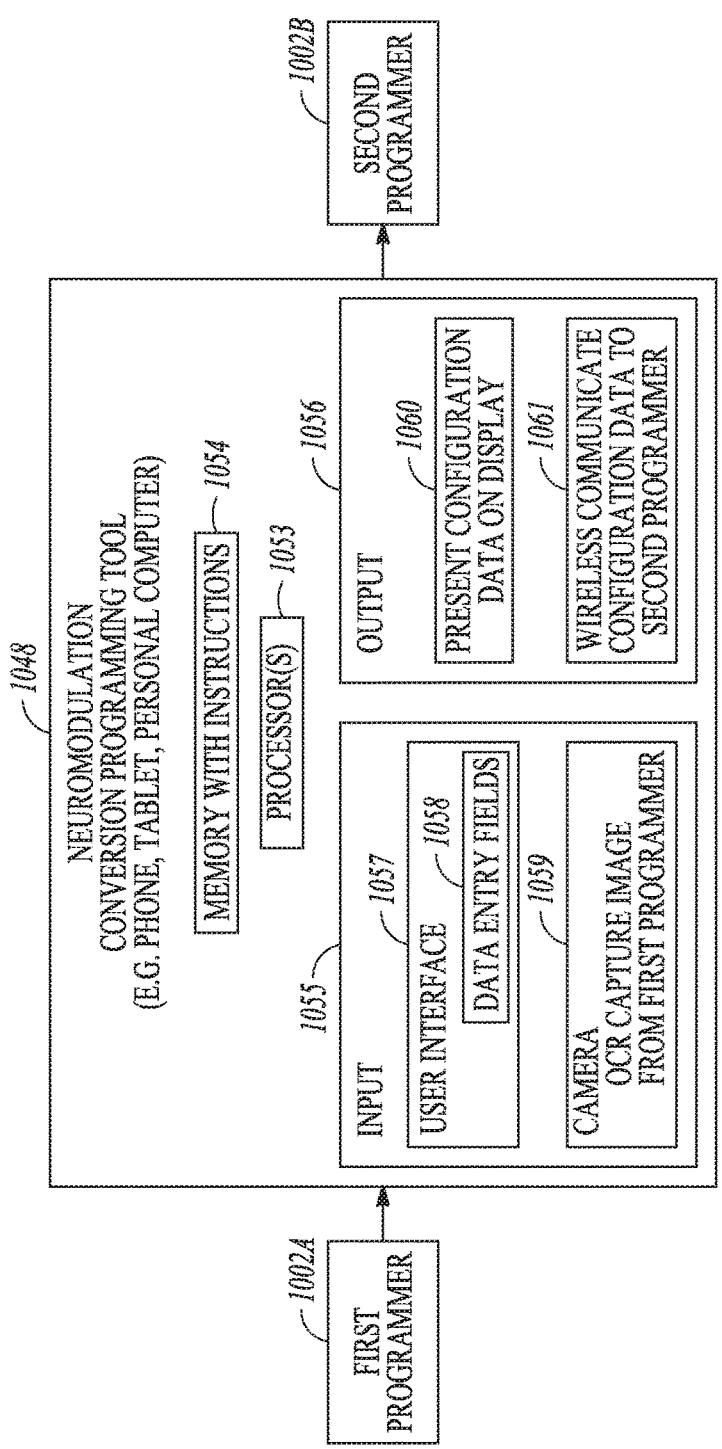
FIG. 10 illustrates various embodiments of the neuromodulation conversion programming tool.

FIG. 10 illustrates various embodiments of the neuromodulation conversion programming tool. The tool implemented by an electronic device (e.g. a personal computer such as a laptop computer, or mobile device such as a smartphone or tablet). The electronic device has at least one processor 1053 and memory 1054 with instruction that are executed by the at least one processor to perform the functions performed by the tool. The electronic device includes input(s) 1055 and output(s) 1056. A user interface 1057 may be used with the input(s). For example, data entry field(s) 1058 may be displayed on the display of the electronic device, and values for those data entry fields may be entered using a keyboard, pointing device (e.g. mouse), touchscreen controls (including virtual keyboard on the touch screen, etc.). Thus, for example, a user may read at least some of the data (e.g. at least some of impedance or therapy data) from the first programmer 1002A and enter them into corresponding data entry fields 1058 for processing by the neuromodulation conversion programming tool. Some embodiments may use a camera 1059 of the electronic device to capture an image of one or more programming screens on the first programmer. The captured image(s) may be processed (e.g. object character recognition) to automatically enter at least some of the data (e.g. at least some or all of impedance or therapy data) into the neuromodulation conversion programming tool. The automatically entered values may be displayed on a display of the electronic device that is configured to operate as the neuromodulation programming tool for review by the user, and may also be edited by the user. Some embodiments may be implemented with a first programmer 1002A that is capable of communicating at least some of the information (model information, contact impedance, modulation parameters) the electronic device that is implementing the neuromodulation conversion programming tool. However, the first neuromodulator and first programmer may be legacy devices from other manufacturers that are not designed to communicate this information to the neuromodulation programming tool.

The output(s) 1056 may simply include the display (e.g. touch screen) of the electronic device that is implementing the neuromodulation conversion programming tool which can be used to present the configuration data 1060. The user may read the converted values, and enter them into the second programmer 1002B. In some embodiments, the neuromodulation programming tool is configured to communicate at least some of the data to the second programmer 1002B. The communication may involve wireless communication to the second programmer through a neuromodulation open source system.

Figure 11:
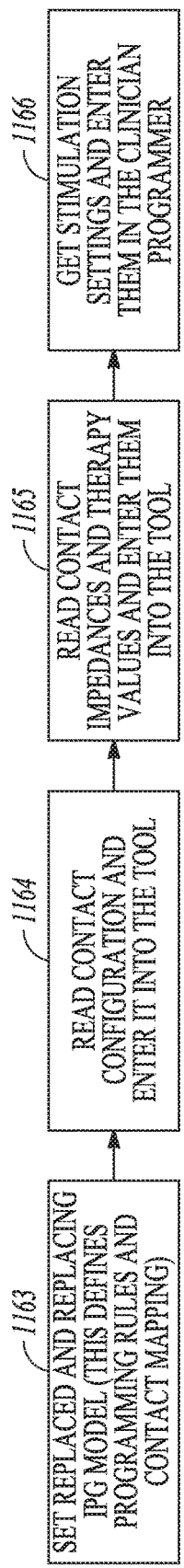
FIG. 11 illustrates, by way of example and not limitation, a process for using the neuromodulation conversion programming tool.

FIG. 11 illustrates, by way of example and not limitation, a process for using the neuromodulation conversion programming tool implemented using the electronic device. At 1162, the neuromodulator model information (e.g. name or number) may be entered for both the first neuromodulator (which also may be referred to as IPG), which is to be replaced, and the second neuromodulator, which is to replace the first neuromodulator. The neuromodulation conversion programming tool is configured to define the programming rules and contact mapping specific to the model of the neuromodulator. The programming rules may convert between the different contact numbering, port numbering, number of contacts per port, and the like. At 1163, contact configuration information may be read or otherwise obtained (e.g. camera capture and object character recognition) from the first programmer and entered into the neuromodulation conversion programming tool. The contact configuration may include, for each contact, Off, Anodic or Cathodic, and may further includes a percentage of total anodic or cathodic contribution. At 1165, contact impedances and therapy values may be read or otherwise obtained (e.g. camera capture and object character recognition) and entered into the neuromodulation conversion programming tool. The neuromodulation conversion programming tool processes the entered data, converting it to stimulation settings for the second neuromodulator. Use of this tool makes replacements more accessible as it might be used by personal with few or no knowledge about Ohms law or DBS stimulation programming (i.e., less support from DBS specialists). At 1166, the stimulation settings are obtained and entered in to the second programmer (e.g. clinician programmer) for the second neuromodulator. The stimulation settings may be obtained by reading the display of the neuromodulation conversion programming tool, or may be obtained by communicating the stimulation settings to the second programmer. For example, settings may be communicated to the second programmer through an interface such as a neuromodulation open system.

Figure 12A:
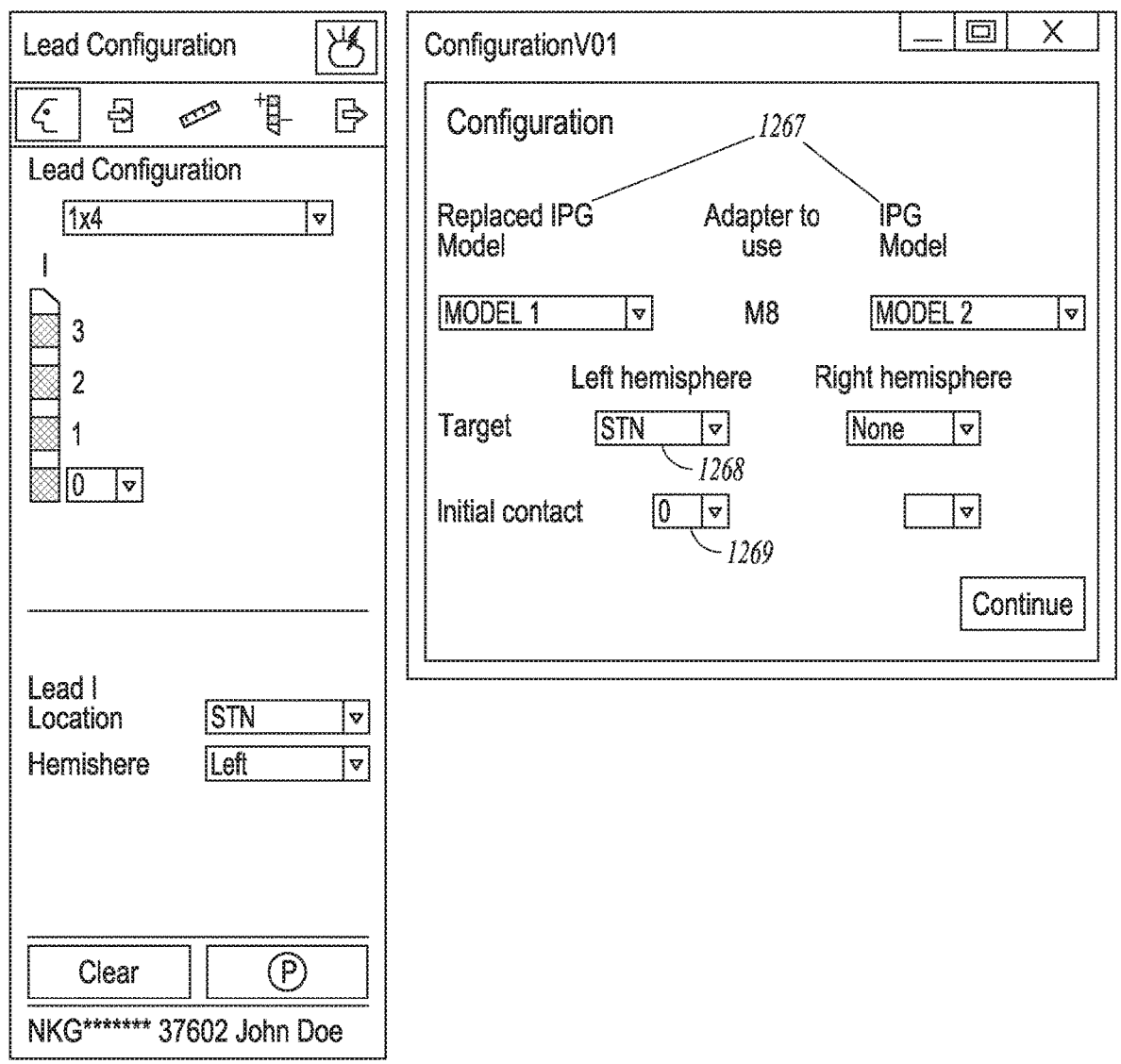
FIG. 12A illustrates a one port lead configuration screen from a first programmer for a first neuromodulator and a lead configuration screen from the neuromodulation conversion programming tool.
Figure 12B:
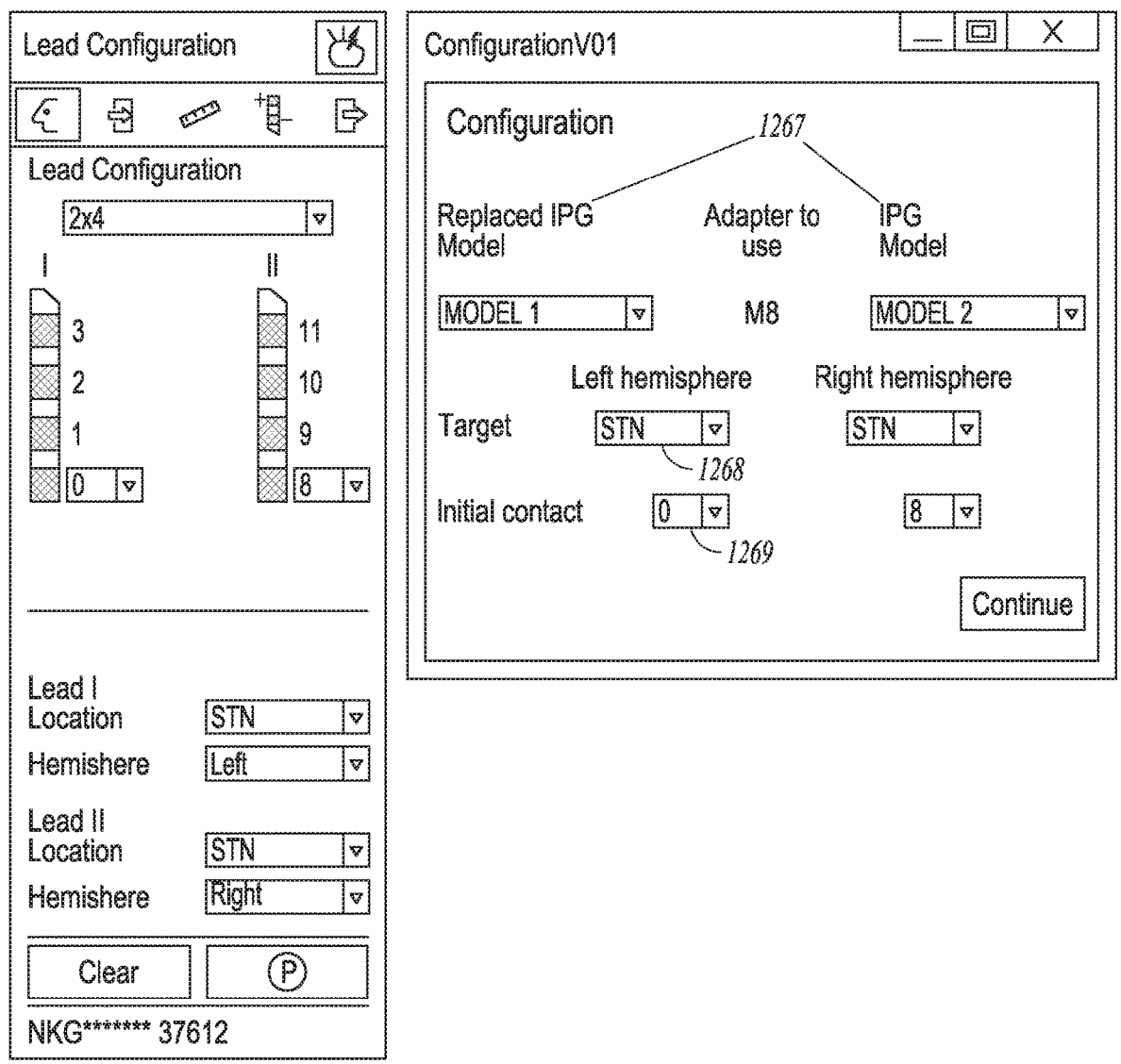
FIG. 12B illustrates a two port lead configuration screen from a first programmer for a first neuromodulator a lead configuration screen from the neuromodulation conversion programming tool, by way of example and not limitation.

FIG. 12A illustrates a one port lead configuration screen from a first programmer for a first neuromodulator and a lead configuration screen from the neuromodulation conversion programming tool, and FIG. 12B illustrates a two port lead configuration screen from a first programmer for a first neuromodulator a lead configuration screen from the neuromodulation conversion programming tool, by way of example and not limitation. Information from the screens for the first neuromodulator may be entered into data fields within the user interface. Model identification 1267 may be entered for both the neuromodulator to be replaced and the replacing neuromodulator. Also the target 1268 may be selected such as from a pull-down menu, and the initial contact 1269 for the first neuromodulator may also be selected from the pull-down menu.

Figure 13A:
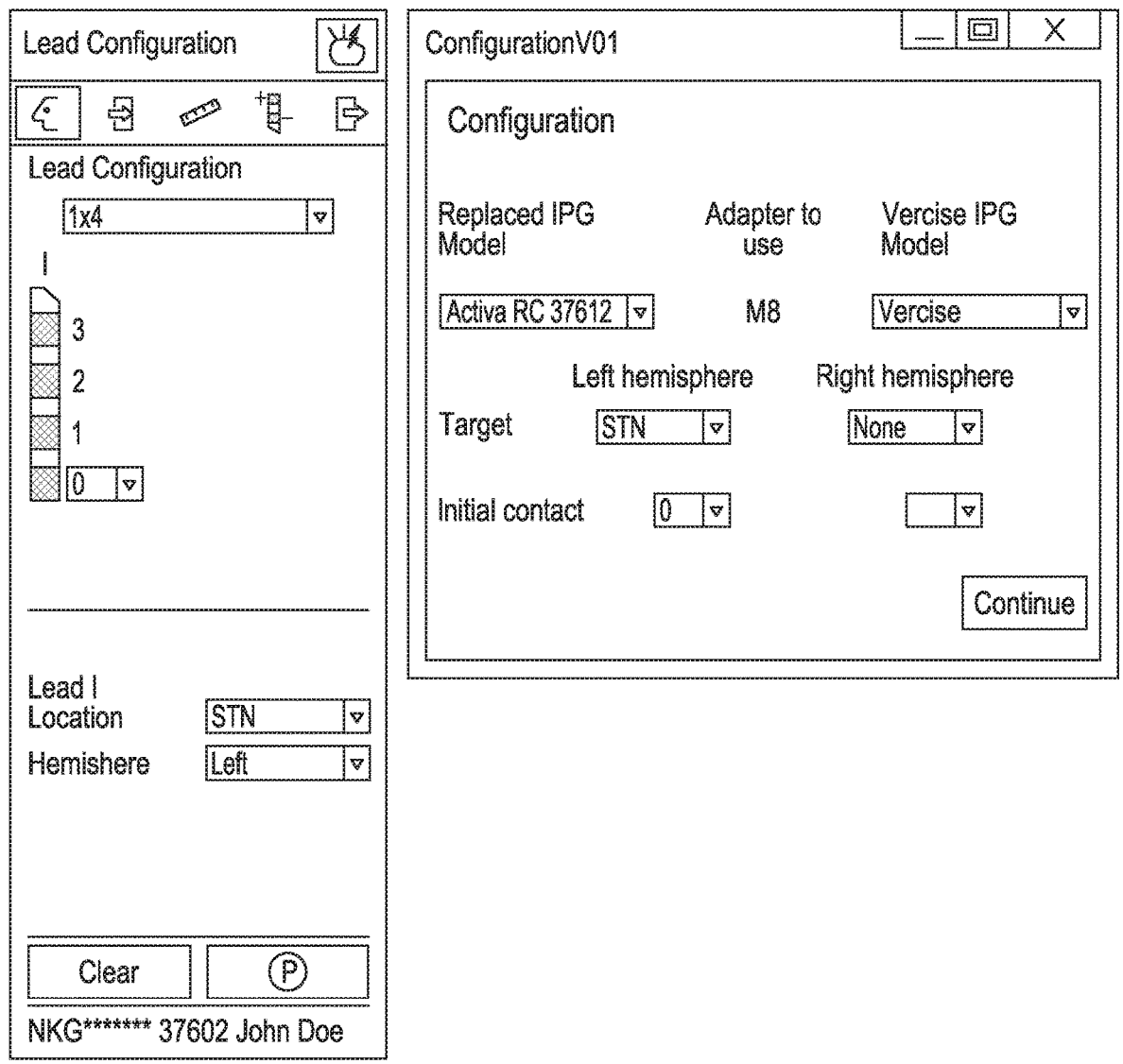
FIG. 13A illustrates a one port therapy setup screen from a first programmer for a first neuromodulator and a therapy setup screen on the neuromodulation conversion programming tool for entering contact configuration values and therapy values.

FIG. 13A illustrates a one port therapy setup screen from a first programmer for a first neuromodulator and a therapy setup screen on the neuromodulation conversion programming tool for entering contact configuration values and therapy values, and FIG. 13B illustrates a two port lead configuration screen from a first programmer for a first neuromodulator and a therapy setup screen on the neuromodulation conversion programming tool for entering contact configuration values and therapy values. These screens may, by way of example and not limitation, form part of the neuromodulation conversion programming tool. The therapy values for a voltage source system (e.g. modulation parameters such as V, μS, and Hz) from the first neuromodulator may be entered into the screen, as well as contact configuration information (anodic or "+"; cathodic or "−") indicating which contacts are active for the first neuromodulator.

Figure 14C:
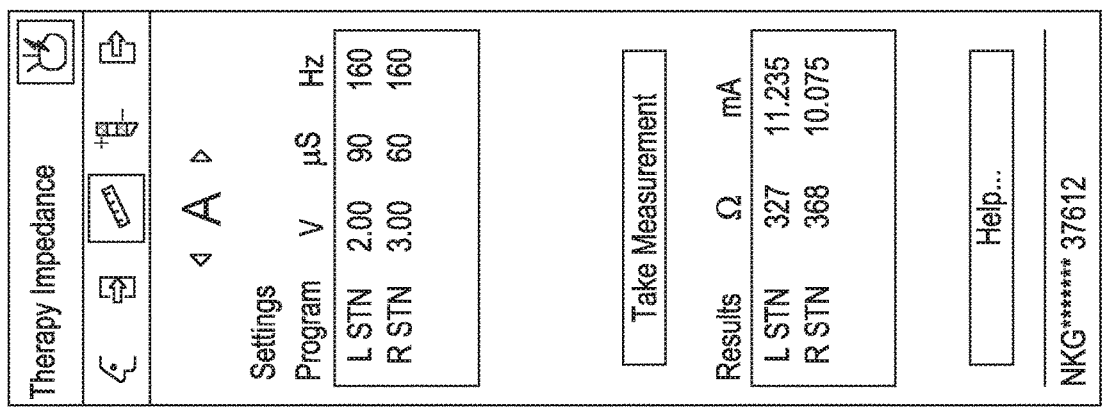
FIG. 14C illustrates a therapy impedance for the therapy delivered by the first modulator, by way of example and not limitation.
Figure 14B:
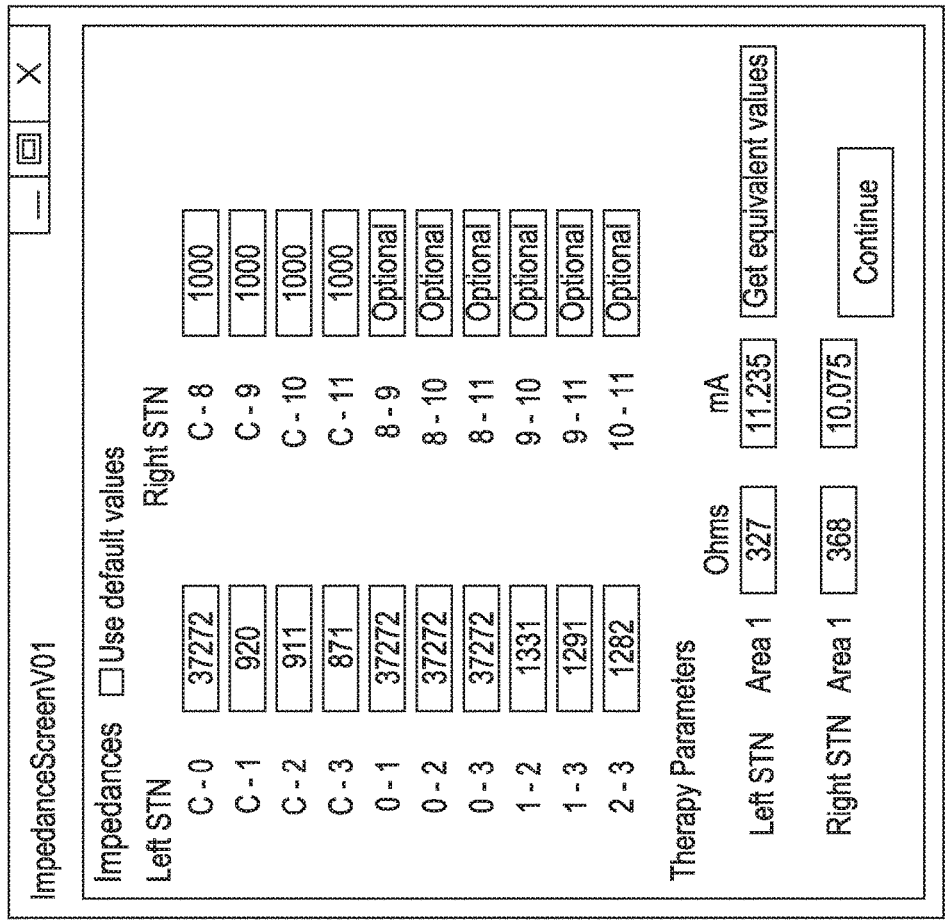
FIG. 14B illustrates an impedance and therapy parameter screen for the first neuromodulator.
Figure 14A:
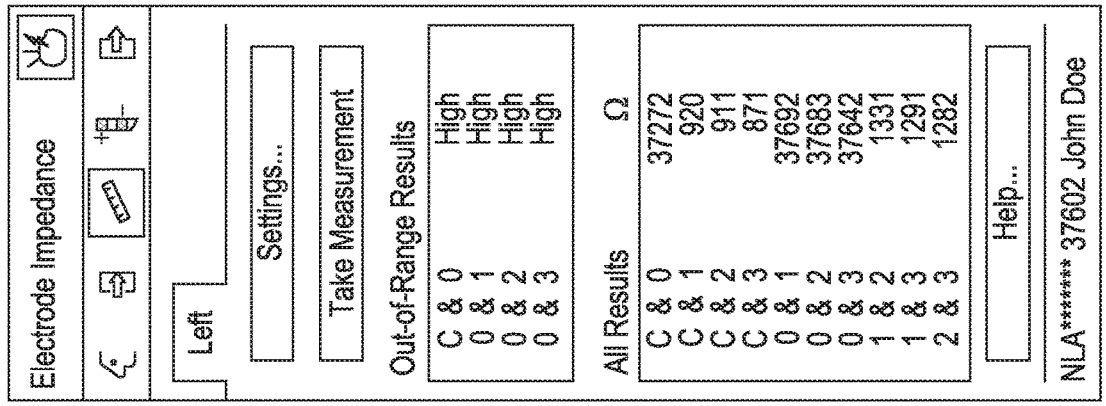
FIG. 14A illustrates an electrode impedance screen for the first modulator where impedances between different pairs of electrodes are identified.

FIG. 14A illustrates an electrode impedance screen for the first modulator where impedances between different pairs of electrodes are identified, FIG. 14B illustrates an impedance and therapy parameter screen for the first neuromodulator, and FIG. 14C illustrates a therapy impedance screen for the therapy delivered by the first modulator wherein the voltage, pulse width and frequency are set, but the impedance and current are determined for the therapy parameters, by way of example and not limitation. This information may be entered into the impedance and therapy parameter screen of the neuromodulation conversion programming tool.

Figure 15A:
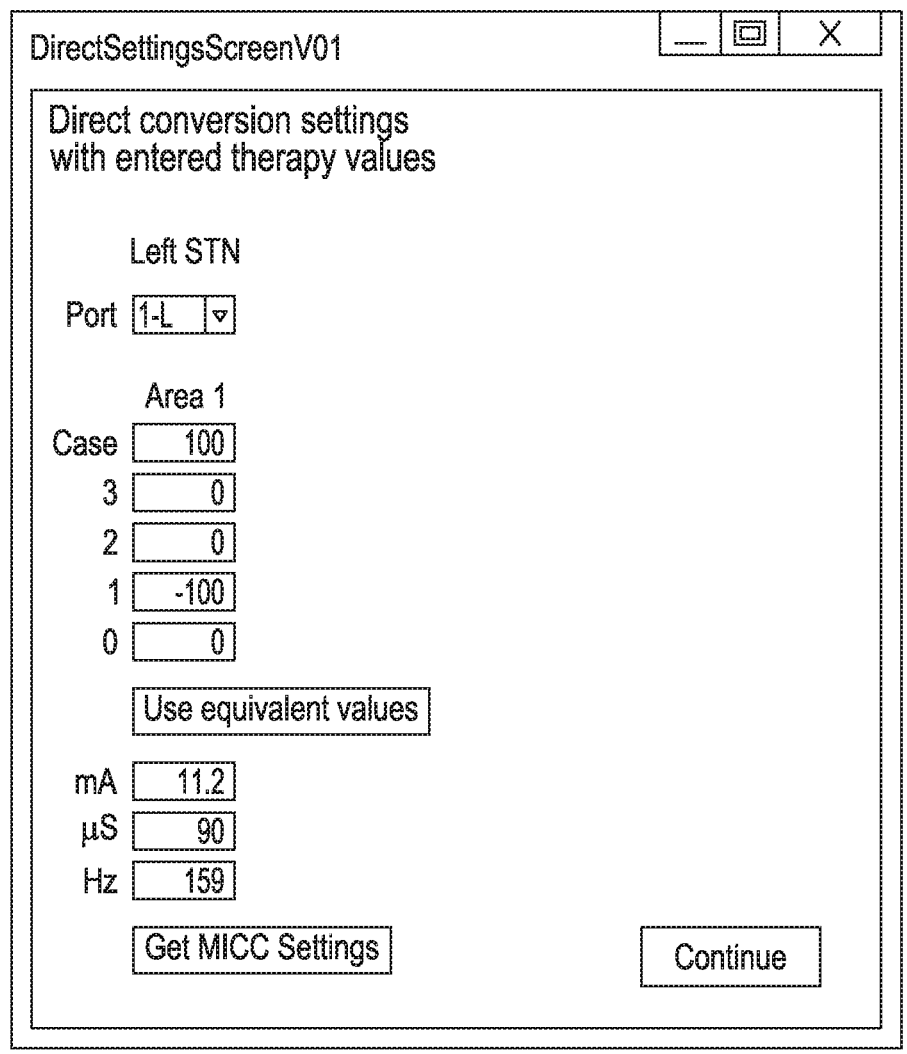
Figure 15B:
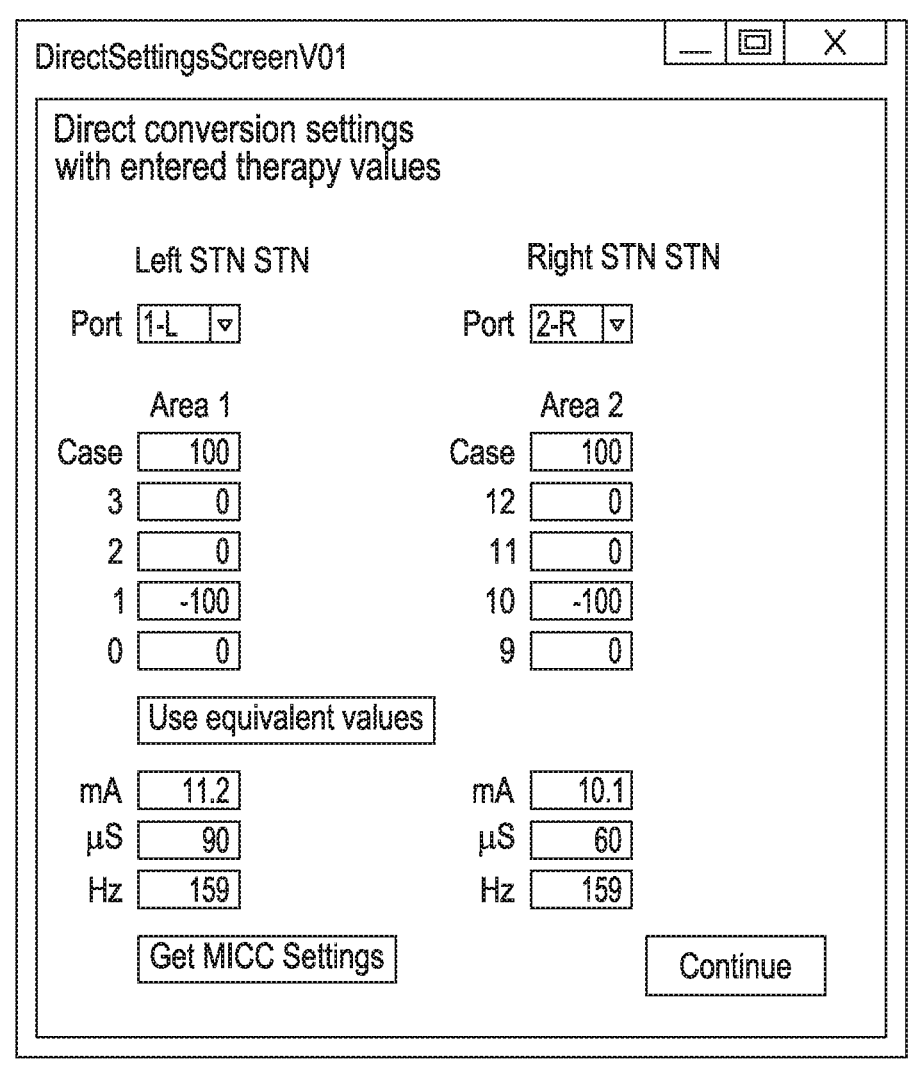

FIG. 15A-15B illustrate examples for a one port and two port system for using direct conversion settings to determine modulation parameter values for the second neuromodulator. The "Use Equivalent Values" feature may be selected to calculate the current, pulse width and frequency of the signal, and the "Get MICC Settings" may be configured to determine the current contributions for each of the active contacts. An active contact may be anodic or cathodic, and may provide a fraction of the total anodic energy or a fraction of the total cathodic energy.

Figure 16:
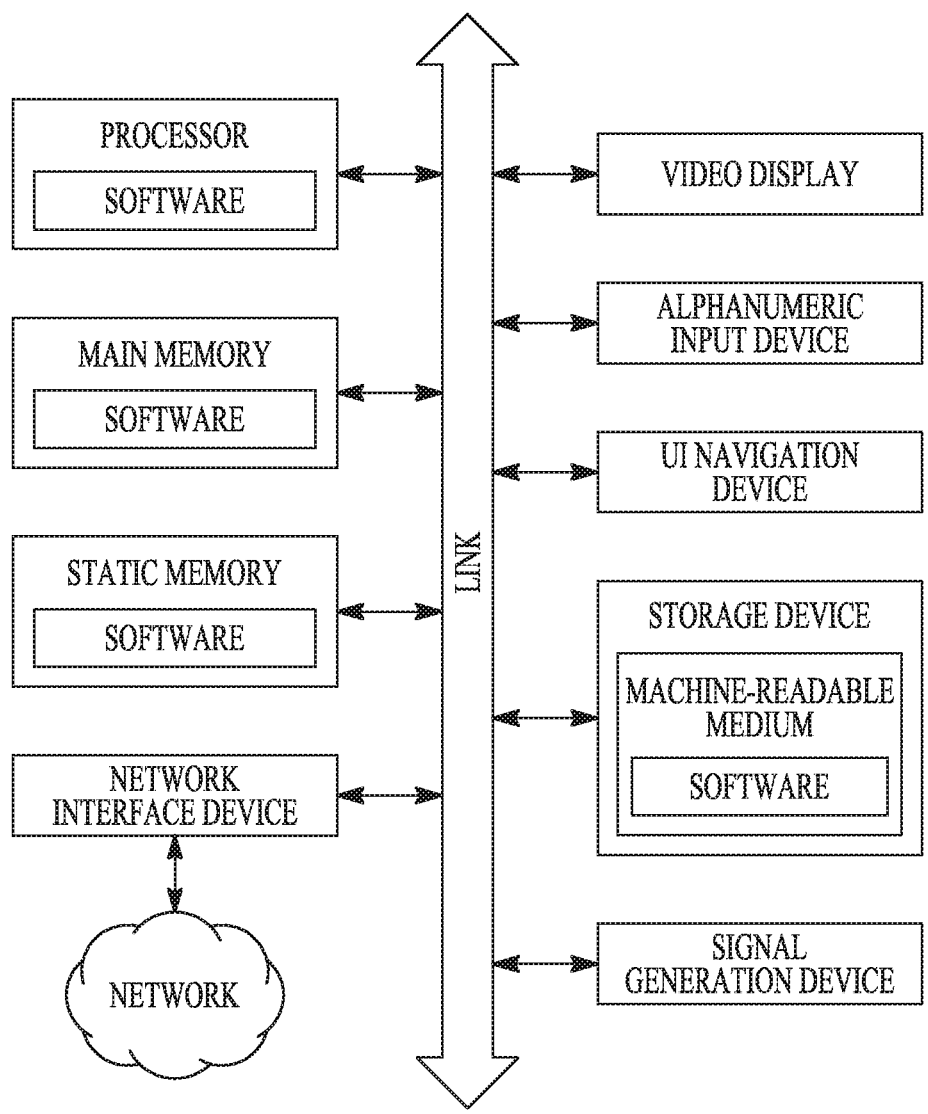
FIG. 16 is a block diagram illustrating a machine in the example form of a computer system, within which a set or sequence of instructions may be executed to cause the machine to perform any one of the methodologies discussed herein.

FIG. 16 is a block diagram illustrating a machine in the example form of a computer system, within which a set or sequence of instructions may be executed to cause the machine to perform any one of the methodologies discussed herein, according to an example embodiment. For example, the machine may be the electronic device implements the neuromodulation conversion programming tool. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a personal computer (PC), a tablet PC, a hybrid tablet, a personal digital assistant (PDA), a mobile telephone, an implantable pulse generator (IPG), an external remote control (RC), a User's Programmer (CP), or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by one or more processors (e.g., a computer) to individually or jointly execute instructions to perform any one or more of the methodologies discussed herein.

An example of a computer system includes at least one processor (e.g., a central processing unit (CPU), a graphics processing unit (GPU) or both, processor cores, compute nodes, etc.), a main memory and a static memory, which communicate with each other via a link (e.g., bus). The computer system may further include a video display unit, an alphanumeric input device (e.g., a keyboard), and a user interface (UI) navigation device (e.g., a mouse). In one embodiment, the video display unit, input device and UI navigation device are incorporated into a touch screen display. The computer system may additionally include a storage device (e.g., a drive unit), a signal generation device (e.g., a speaker), a network interface device, and one or more sensors (not shown), such as a global positioning system (GPS) sensor, compass, accelerometer, or another sensor. It will be understood that other forms of machines or apparatuses (such as IPG, RC, CP devices, and the like) that are capable of implementing the methodologies discussed in this disclosure may not incorporate or utilize every component depicted in FIG. 16 (such as a GPU, video display unit, keyboard, etc.).

The storage device includes a machine-readable medium on which is stored one or more sets of data structures and instructions (e.g., software) embodying or utilized by any one or more of the methodologies or functions described herein. The instructions may also reside, completely or at least partially, within the main memory, static memory, and/or within the processor during execution thereof by the computer system, with the main memory, static memory, and the processor also constituting machine-readable media.

While the machine-readable medium is illustrated in an example embodiment to be a single medium, the term "machine-readable medium" may include a single medium or multiple media (e.g., a centralized or distributed database, and/or associated caches and servers) that store the one or more instructions. The term "machine-readable medium" shall also be taken to include any tangible (e.g., non-transitory) medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions may further be transmitted or received over a communications network using a transmission medium via the network interface device utilizing any one of a number of well-known transfer protocols (e.g., HTTP or Bluetooth®). Examples of communication networks include a local area network (LAN), a wide area network (WAN), the Internet, mobile telephone networks, plain old telephone (POTS) networks, and wireless data networks (e.g., Wi-Fi, 3G, and 4G LTE/LTE-A or 5G networks). The term "transmission medium" shall be taken to include any intangible medium that is capable of storing, encoding, or carrying instructions for execution by the machine, and includes digital or analog communications signals or other intangible medium to facilitate communication of such software.

The above detailed description is intended to be illustrative, and not restrictive. The scope of the disclosure should, therefore, be determined with references to the appended claims, along with the full scope of equivalents to which such claims are entitled.

What is claimed is:

1. A method implemented using a first neuromodulator programmed with a first set of modulation parameter settings to generate at least a first modulation field at one or more targets, the method comprising:
   receiving the first set of modulation parameter settings for the first neuromodulator;
   replacing the first neuromodulator with a second neuromodulator, wherein the first and second neuromodulators are different models that use different neuromodulation field generation technology and that have different programmable parameters to program the different technology;
   determining, using a processor configured to execute a programmed set of instructions and using the first set of modulation parameter settings, a second set of modulation parameter settings for the second neuromodulator to generate at least a second modulation field that is similar to the at least the first modulation field, generated by the first neuromodulator, at the one or more targets;
   programming the second neuromodulator with the second set of modulation parameters; and
   delivering neuromodulation using the second neuromodulator programmed with the second set of modulation parameters,
   wherein the receiving the first set of modulation parameter settings includes:
      using a camera to capture an image from a programmer screen for a programmer of the first neuromodulator wherein the programmer screen includes at least one setting for the first set of modulation parameter settings; and
      automatically recognizing the at least one setting from the image and use the at least one setting from the image in determining the second set of modulation parameter settings for the second neuromodulator.

2. The method of claim 1, wherein:
   the first set of modulation parameter settings includes contact polarity settings to define a first set of active electrodes on at least one implanted lead including polarity for each of the first set of active electrodes, and the second set of modulation parameter settings includes contact polarity settings to define a second set of active electrodes on the at least one implanted lead including polarity for each of the second set of active electrodes;
   the first neuromodulator is configured to implement the programmed first set of modulation parameter settings to deliver electrical energy using the at least one implanted lead to provide the at least the first modulation field;
   the second neuromodulator is configured to implement the second set of modulation parameter settings to deliver electrical energy using the at least one implanted lead to provide the at least the second modulation-field; and
   the determining the second set of modulation parameter settings includes determining the second set of modulation parameter settings that cause the at least the second modulation-field to have a similar size and shape to the at least the first modulation field.

3. The method of claim 1, wherein:
   the first neuromodulator includes a voltage source for use to provide voltage source modulation;
   the second neuromodulator includes a current source for use to provide current source modulation; and
   the determining the second set of modulation parameter settings includes determining modulation parameter settings for the current source modulation based on parameter settings for voltage source modulation.

4. The method of claim 3, wherein the first neuromodulator has one voltage source for use to provide the voltage source modulation, and the second neuromodulator includes multiple current sources for use to provide the current source modulation.

5. The method of claim 1, wherein the first set of modulation parameter settings determine electrode polarity to provide more than one anode or more than one cathode.

6. The method of claim 1, wherein the determining the second set of modulation parameter settings includes implementing an app on a tablet or a phone to determine the second set of modulation parameter settings for the second neuromodulator based on the first set of modulation parameter settings for the first neuromodulator.

7. The method of claim 1, wherein the determining the second set of modulation parameter settings includes implementing a program on a personal computer to determine the second set of modulation parameter settings.

8. The method of claim 1, further comprising receiving via a user interface model identification for the first neuromodulator and model identification for the second neuromodulator.

9. The method of claim 1, further comprising receiving via a user interface contact impedance data.

10. The method of claim 1, wherein the receiving the first set of modulation parameter settings includes receiving via a user interface contact configuration data.

11. The method of claim 1, wherein the receiving the first set of modulation parameter settings includes receiving via a user interface therapy values.

12. The method of claim 1, further comprising presenting the second set of modulation parameter settings to a user via a display on a mobile device for use by the user for entering into a neuromodulator programmer used to program the second neuromodulator, wherein the mobile device includes a phone or tablet or personal computer.

13. The method of claim 1, further comprising wirelessly communicating the second set of modulation parameter settings to a neuromodulator programmer.

14. A method implemented using a first neuromodulator programmed with a first set of modulation parameter settings to generate at least a first modulation field at one or more targets, the method comprising:
  receiving the first set of modulation parameter settings for the first neuromodulator;
  replacing the first neuromodulator with a second neuromodulator, wherein the first and second neuromodulators are different models that use different neuromodulation field generation technology and that have different programmable parameters to program the different technology;
  determining, using a processor configured to execute a programmed set of instructions and using the first set of modulation parameter settings, a second set of modulation parameter settings for the second neuromodulator to generate at least a second modulation field that is similar to the at least the first modulation field, generated by the first neuromodulator, at the one or more targets;
  programming the second neuromodulator with the second set of modulation parameters; and
  delivering neuromodulation using the second neuromodulator programmed with the second set of modulation parameters,
  wherein the receiving the first set of modulation parameter settings includes:
    using a camera to capture an image from a programmer screen for a programmer of the first neuromodulator wherein the programmer screen includes at least one setting for the first set of modulation parameter settings; and
  automatically recognizing the at least one setting from the image and use the at least one setting from the image in determining the second set of modulation parameter settings for the second neuromodulator,
    wherein the first neuromodulator includes a voltage source for use to provide voltage source modulation, the second neuromodulator includes a current source for use to provide current source modulation, and the determining the second set of modulation parameter settings includes determining modulation parameter settings for the current source modulation based on parameter settings for voltage source modulation, and
  wherein the method further includes presenting the second set of modulation parameter settings to a user via a display on a mobile device for use by the user for entering into a neuromodulator programmer used to program the second neuromodulator, wherein the mobile device includes a phone or tablet or personal computer.

15. The method of claim 14, wherein the first set of modulation parameter settings determine electrode polarity to provide more than one anode or more than one cathode.

16. The method of claim 14, wherein the determining the second set of modulation parameter settings includes implementing an app on a tablet or a phone to determine the second set of modulation parameter settings for the second neuromodulator based on the first set of modulation parameter settings for the first neuromodulator.

17. The method of claim 14, wherein the determining the second set of modulation parameter settings includes implementing a program on a personal computer to determine the second set of modulation parameter settings.

18. A method implemented using a first neuromodulator programmed with a first set of modulation parameter settings to generate at least a first modulation field at one or more targets, the method comprising:
  receiving the first set of modulation parameter settings for the first neuromodulator;
  replacing the first neuromodulator with a second neuromodulator, wherein the first and second neuromodulators are different models that use different neuromodulation field generation technology and that have different programmable parameters to program the different technology;
  determining, using a processor configured to execute a programmed set of instructions and using the first set of modulation parameter settings, a second set of modulation parameter settings for the second neuromodulator to generate at least a second modulation field that is similar to the at least the first modulation field, generated by the first neuromodulator, at the one or more targets;
  programming the second neuromodulator with the second set of modulation parameters; and
  delivering neuromodulation using the second neuromodulator programmed with the second set of modulation parameters,
  wherein the receiving the first set of modulation parameter settings includes:
    using a camera to capture an image from a programmer screen for a programmer of the first neuromodulator wherein the programmer screen includes at least one setting for the first set of modulation parameter settings; and
  automatically recognizing the at least one setting from the image and use the at least one setting from the image in determining the second set of modulation parameter settings for the second neuromodulator,
    wherein the determining the second set of modulation parameter settings includes implementing an app on a tablet or a phone to determine the second set of modulation parameter settings for the second neuromodulator based on the first set of modulation parameter settings for the first neuromodulator, and
wherein the method further includes receiving via a user interface:
   model identification for the first neuromodulator and model identification for the second neuromodulator, or
   contact impedance data.

19. The method of claim 18, wherein the receiving the first set of modulation parameter settings includes receiving via a user interface contact configuration data.

20. The method of claim 18, wherein the receiving the first set of modulation parameter settings includes receiving via a user interface therapy values.

* * * * *